(12) United States Patent
Bernard et al.

(10) Patent No.: US 12,213,892 B2  
(45) Date of Patent: Feb. 4, 2025

(54) EXPANSIBLE INTERVERTEBRAL IMPLANT

(71) Applicant: LDR Medical, S.A.S., Sainte-Savine (FR)

(72) Inventors: Pierre Bernard, Bordeaux (FR); Herve Chataigner, Bussieres (FR); Craig Chebuhar, Marietta, GA (US); Alexander Kirgis, Krailling (DE); Ross Sherban, Clarence, NY (US); Samuel Lequette, Pessac (FR); Emmanuel Bougere, Bordeaux (FR); Aymeric Fresneau, Bordeaux (FR); Nicolas Roche, Saint Medard en Jalles (FR)

(73) Assignee: LDR Medical, S.A.S. (FR)

( * ) Notice: Subject to any disclaimer, the term of this patent is extended or adjusted under 35 U.S.C. 154(b) by 0 days.

(21) Appl. No.: 17/888,895

(22) Filed: Aug. 16, 2022

(65) Prior Publication Data

US 2022/0387182 A1 Dec. 8, 2022

Related U.S. Application Data

(63) Continuation of application No. 16/737,712, filed on Jan. 8, 2020, now Pat. No. 11,432,944, which is a (Continued)

(30) Foreign Application Priority Data

Oct. 27, 2016 (FR) ........................... 1660472

(51) Int. Cl.  
A61F 2/44 (2006.01)  
A61F 2/30 (2006.01)  
(Continued)

(52) U.S. Cl.  
CPC .......... A61F 2/447 (2013.01); A61F 2/30771 (2013.01); A61F 2/4455 (2013.01); (Continued)

(58) Field of Classification Search  
CPC ...... A61F 2/447; A61F 2/4455; A61F 2/4611; A61F 2/4601; A61F 2002/30471; (Continued)

(56) References Cited

U.S. PATENT DOCUMENTS 11,432,944 B2 * 9/2022 Bernard ................. A61F 2/4455  
2013/0023994 A1 * 1/2013 Glerum ................... A61F 2/447  
623/17.16

(Continued)

*Primary Examiner* — Marcela I. Shirsat  
(74) *Attorney, Agent, or Firm* — Sheridan Ross P.C.

(57) ABSTRACT

Various embodiments of an intervertebral implant comprise a body extending longitudinally along a primary axis, a baseplate, a plurality of elongated arms having a vertebral support surface, the arms being articulated such that the implant has a folded-back position in which the arms are close to each other, and a deployed position in which the arms are moved away from each other, and expansion means between the folded-back and deployed positions, comprising at least two branches pivotably mounted relative to each other and attached to the elongated arms by guide means such that translation of the expansion means parallel to the primary axis causes pivoting of the branches and moves the arms away from each other.

19 Claims, 21 Drawing Sheets

Related U.S. Application Data continuation of application No. 15/796,732, filed on Oct. 27, 2017, now Pat. No. 10,561,502.

(51) Int. Cl.
*A61F 2/42* (2006.01)
*A61F 2/46* (2006.01)

(52) U.S. Cl.
CPC ... *A61F 2/4611* (2013.01); *A61F 2002/30362* (2013.01); *A61F 2002/30429* (2013.01); *A61F 2002/30471* (2013.01); *A61F 2002/30538* (2013.01); *A61F 2002/30553* (2013.01); *A61F 2002/30556* (2013.01); *A61F 2002/30579* (2013.01); *A61F 2002/30593* (2013.01); *A61F 2002/30828* (2013.01); *A61F 2002/30904* (2013.01); *A61F 2/4261* (2013.01); *A61F 2/4601* (2013.01); *A61F 2/4603* (2013.01); *A61F 2/4609* (2013.01); *A61F 2002/4627* (2013.01); *A61F 2002/4629* (2013.01); *A61F 2002/4687* (2013.01)

(58) Field of Classification Search
CPC .. A61F 2002/30538; A61F 2002/30553; A61F 2002/30556; A61F 2002/30579; A61F 2002/4624; A61F 2002/4627; A61F 2002/4629; A61F 2002/30362; A61F 2002/30904
USPC .............................................. 623/17.11–17.16
See application file for complete search history.

(56) References Cited

U.S. PATENT DOCUMENTS

2014/0039622 A1* 2/2014 Glerum .................. A61F 2/447
623/17.15
2015/0148908 A1* 5/2015 Marino .................. A61F 2/442
623/17.16
2017/0000622 A1* 1/2017 Thommen ............ A61F 2/4425

* cited by examiner

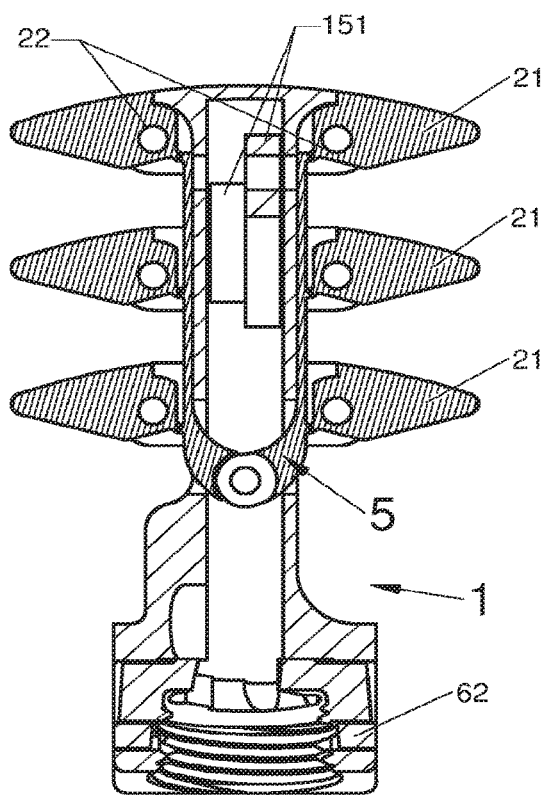
Figure 1A
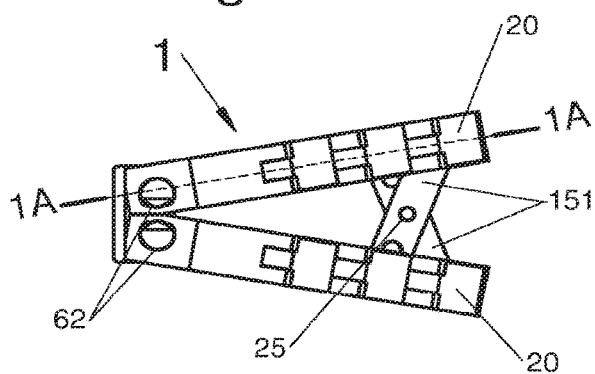
Figure 1B
Figure 1C
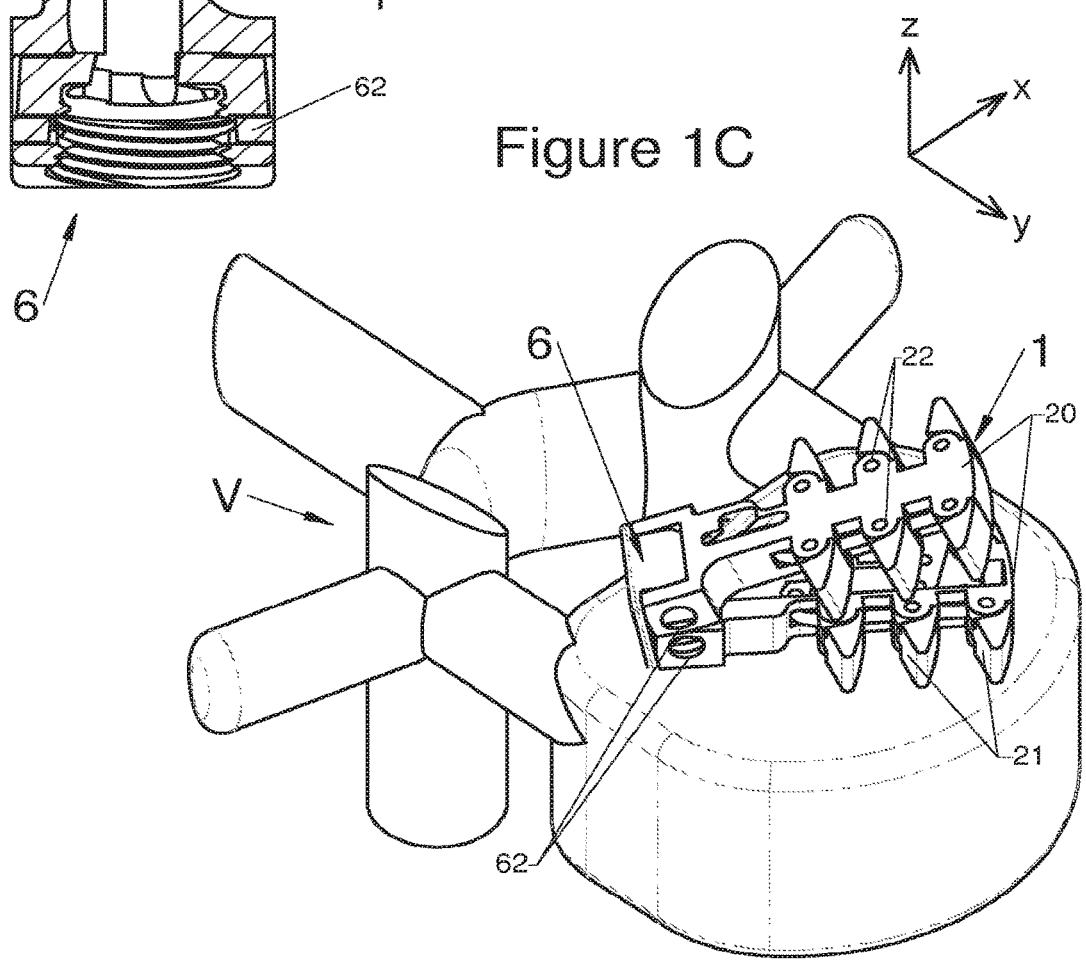

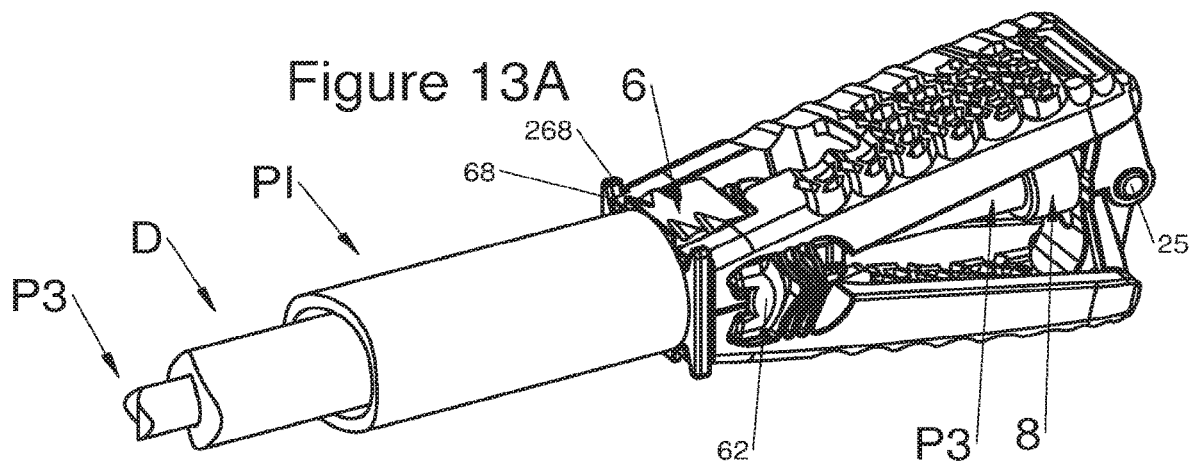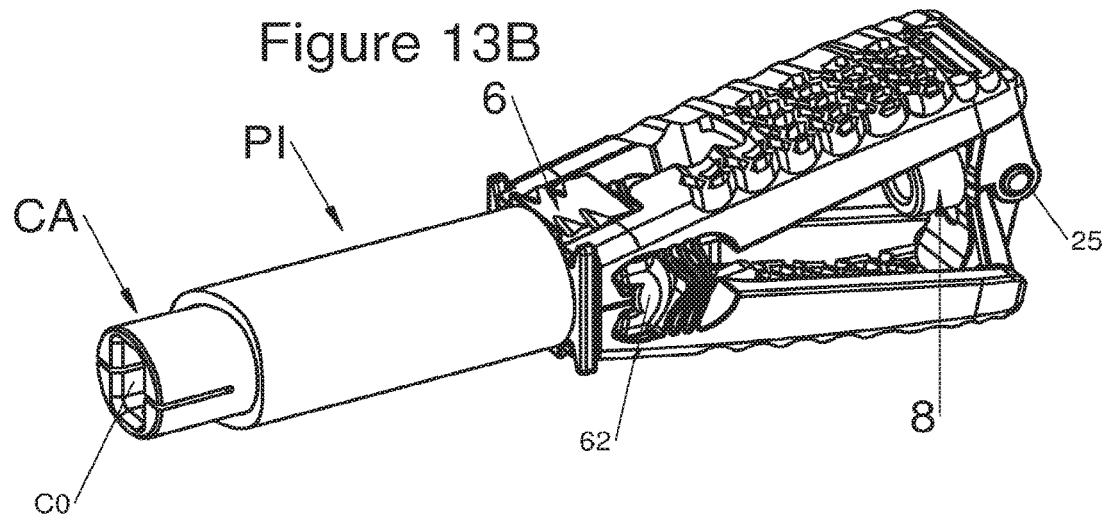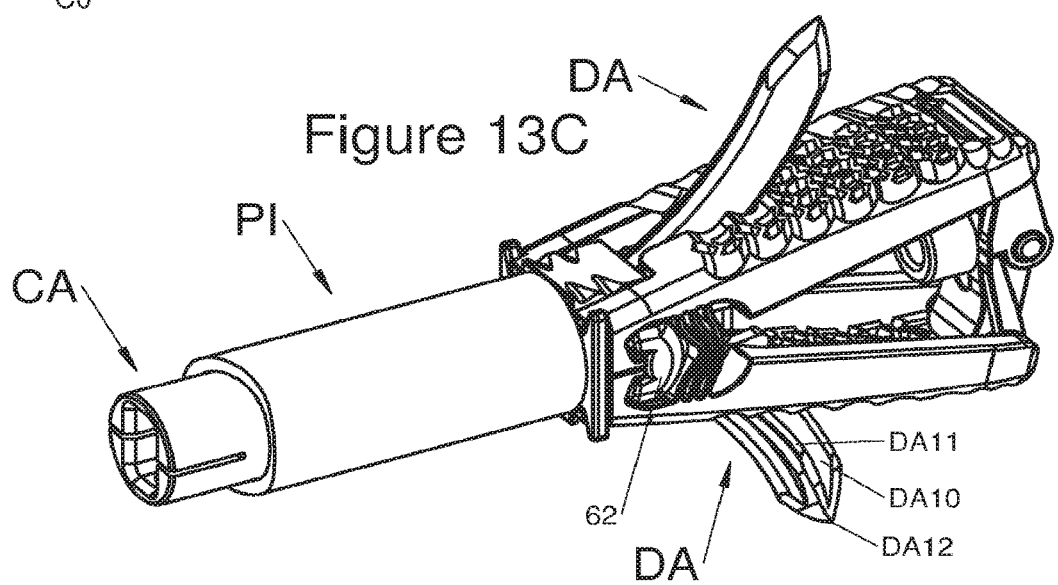

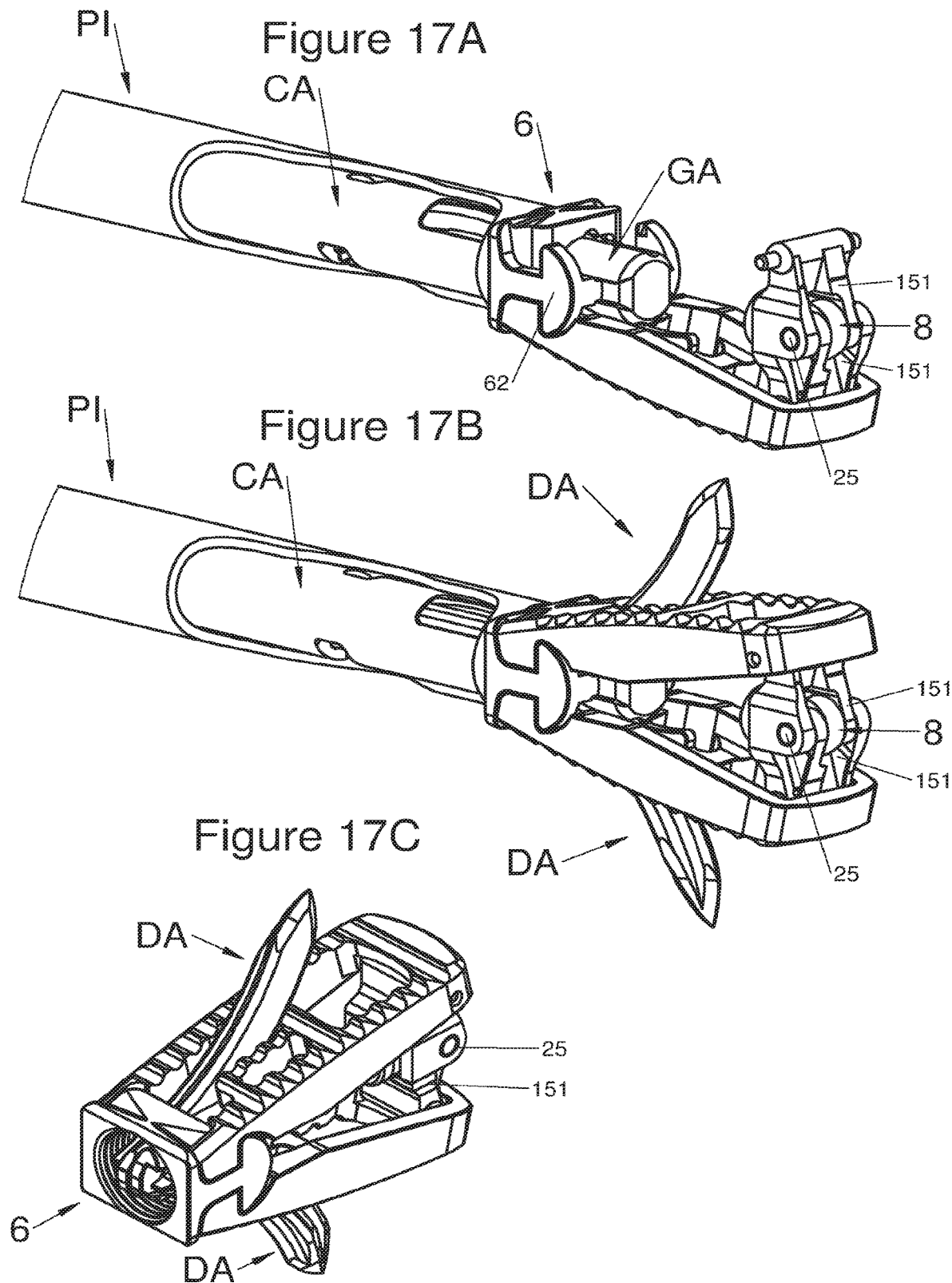

EXPANSIBLE INTERVERTEBRAL IMPLANT

CROSS-REFERENCE TO RELATED APPLICATIONS

This application is a continuation of U.S. application Ser. No. 16/737,712, filed Jan. 8, 2020, now U.S. Pat. No. which is a continuation of U.S. Application No. 15/796,732, filed Oct. 27, 2017, now U.S. Pat. No. 10,561,502 which claims priority under 35 U.S.C. § 119 to French Patent Application No. FR1660472 filed in FRANCE on Oct. 27, 2016, all of which are incorporated herein by reference.

BACKGROUND

The present disclosure relates to the field of vertebral implants and in general to the field of implants intended to be implanted between two vertebrae to at least partially supplant an intervertebral disc. The present disclosure relates more particularly to an expansible intervertebral implant, of corpectomy cage or intersomatic cage type.

Intervertebral implants are implanted between two adjacent vertebrae to allow insertion and growth of bone tissue grafts (or substitute) in the disc space to create arthrodesis (fusion of two vertebrae). The intervertebral space, after the cage is placed, is generally filled with autologous cancellous bone or adapted bone substitutes.

Various arthrodesis techniques are known from the prior art, based on various types of implants, such as for example corpectomy cages or intersomatic cages inserted in place of a disc to promote bone growth (or arthrodesis) and secure at least two vertebrae together. Such devices are for example illustrated in French patent application FR1651637 which describes intersomatic cages for supplanting an intervertebral disc. Other examples of implants are described, for example, in the following patents or patent applications: U.S. Pat. Nos. 6,447,546, 7,291,170, 7,594,931, 8,241,359, 8,343,219, 8,409,288, 8,617,245, 9,039,774, 9,044,337, 9,173,745, US20150045893A1, US20150127107A1, US20150209089A1 and US20150320568A1.

A frequent problem in the field of vertebral implants and especially of corpectomy cages or intervertebral cages relates to the ability to maximize the stability of such implants so as to cover a volume which most closely approaches the volume occupied by the affected vertebral disc. Implants of the prior art therefore generally have substantial volume, which makes their implantation highly invasive for the patient.

A solution used for reducing the size of the implants during their implantation has been the use of expansible cages as for example described in patent application EP1699389. Such cages, once they are implanted, are deployed by the surgeon, to cover a volume approaching the volume of an intervertebral disc, while having a profile for following the lordosis of the vertebral column, thereby improving comfort for the patient and stability of the cage. Nevertheless, this type of expansible cages has a certain number of drawbacks. Indeed, during their expansion, the surgeon should exert inordinate pressure on the implant given that its expansion is simultaneously ensured on two axes orthogonal with each other. Moreover, the prior art implants are complex, deploy only in a single direction (in height, or in lordosis, or in surface area) and without stabilizing elements intrinsic to said implants. This imposes a difficulty for the surgeon in complying with a specific lordosis. In fact, this type of cage does not allow a considerable deployment amplitude and the expansion in height may therefore be insufficient for effectively restoring the height and the desired intervertebral lordosis. The expansion in surface area may be insufficient to provide support for the implant on the peripheral zones of the vertebral endplate, which is generally stronger, because the implant will remain positioned over the more central zones, causing a greater risk of collapse of the implant into the vertebral body. While generally, a distribution of the support points over a larger surface will allow better stabilization of the vertebral bodies with respect to each other.

In this context it is interesting to propose an implantable and easily expansible implant solution, which is reliable and non-invasive, adaptable in different instances of lordosis and limits risk of embrittling the adjacent vertebral structures.

SUMMARY OF THE DISCLOSURE

The subject of the present disclosure is to propose an intervertebral implant to eliminate at least some of the drawbacks of the prior art by proposing an intervertebral implant having limited invasivity and having improved stability and reliability, easier expansion for the surgeon and optionally imposing lordosis.

To this end, various embodiments of the disclosure relate to an intervertebral implant comprising a body extending longitudinally along a primary axis, between a proximal end and a distal end, the intervertebral implant includes:
  a baseplate at the proximal end,
  a plurality of elongated arms along the primary axis and each including at least one vertebral support surface, the arms being articulated at least on the baseplate such that the implant comprises on the one hand a folded-back position in which the arms are close to each other, and on the other hand a deployed position in which the arms are moved away from each other along at least one secondary axis and/or at least one tertiary axis, the primary, secondary and tertiary axes being substantially orthogonal to each other;
  expansion means of the implant between the folded-back and deployed positions, comprising at least two branches pivotably mounted one relative to the other and attached to the elongated by at least guide means, such that translation of the expansion means parallel to the primary axis causes pivoting of the branches one relative to the other and moves the arms away from each other, along the secondary axis and/or the tertiary axis.

According to another feature, the expansion means comprise at least one insert which may be screwed through the baseplate to cause translation of the expansion means relative to the body of the implant during deployment of the elongated arms.

According to another feature, pivoting of the branches one relative to the other occurs around at least one pivoting axis oriented parallel to the secondary axis to move away the elongated arms along this axis and enable expansion of the width of the implant.

According to another feature, the expansion means of the implant also comprise expansion means in height of the implant, along an axis parallel to the tertiary axis, using the guide means comprising inner surfaces of the arms which are non-parallel to each other and divergent in the direction of the distal end, such that the arms are moved away from each other along the tertiary axis during translation of the expansion means along the primary axis.

According to another feature, pivoting of the branches one relative to the other occurs around at least one pivoting axis oriented parallel to the tertiary axis to move the elongated arms away along this axis and enable expansion of the height of the implant.

According to another feature, the expansion means of the implant also comprise expansion means in width of the implant, along an axis parallel to the secondary axis.

According to another feature, the expansion means in width of the implant comprise flexible blades secured to the distal end of the arms of the implant and slidably mounted relative to the rest of the arms, but connected to the expansion means in height, such that actuation of the translation causes sliding and deformation of the flexible blades, causing expansion of the width covered by the implant.

According to another feature, the expansion means in width of the implant comprise pivot arms pivotably mounted on a pivoting axis and with respect to the body between the folded-back position in which the pivot arms are substantially parallel to the pivoting axis and border the body, and the deployed position in which the arms are moved away from the body and non-parallel to the pivoting axis so as to deploy said implant along the secondary axis.

According to another feature, the baseplate comprises an articulation capable of joining the arms together on the proximal end of the body, the articulation forming a ring segment.

According to another feature, the implant comprises articulations articulating the baseplate and the elongated arms between the folded-back position and the deployed position.

According to another feature, the articulations form reciprocal coupling means between the baseplate and at least one of the elongated arms.

According to another particular feature, the articulations comprise at least one plate articulated at the same time on the baseplate and on the proximal end of at least one elongated arm.

According to another feature, the articulations form reciprocal coupling means, on the one hand, between the plate and the baseplate, and on the other hand, between the plate and the proximal end of at least one of the elongated arms.

According to another feature, the guide means comprise at least one projection disposed on the expansion means, and at least one groove disposed on at least one of the elongated arms, such that the groove guides the projection along the body during deployment of the elongated arms.

According to another feature, the expansion means comprise at least one hooking means with at least one instrumentation and connected to the branches so as to cause translation of the expansion means relative to the body of the implant during deployment of the elongated arms.

According to another feature, the insert is configured to dissociate itself into at least two fragments, forming said branches, to cause translation of the expansion means with respect to the body of the implant during deployment of the elongated arms.

According to another feature, the branches are disposed on the distal end of the body of the implant and comprise at least one projecting portion for anchoring said implant on at least one vertebra.

According to another feature, the implant comprises at least one anchoring device capable of passing through a passage passing through at least one portion of said implant between a periphery of the implant and at least one vertebra and fixing said implant on said vertebra.

According to another feature, the baseplate comprises at least one guide groove adapted to at least partially guide the anchoring device.

According to another feature, the baseplate comprises at least one orifice adapted to at least partially receive an anchoring guide of the anchoring device.

Another aim of the present disclosure is to propose implantation instrumentation allowing at least a portion of the drawbacks of the prior art to be mitigated, by proposing instruments configured for implanting at least one intervertebral implant according to one of the features of various embodiments. To this end, according to certain features, the instrumentation allows facilitating and accelerating the implantation of an intervertebral implant, while improving, on the one hand, the stability; and the reliability of the implantation, and on the other hand by reducing the invasiveness of the implantation and the costs of the necessary instruments.

To this end, the disclosure relates to instrumentation for the implantation of at least one intervertebral implant according to one of the features of various embodiments, between at least two vertebrae. The instrumentation comprises at least the following instruments:

an implant holder tube capable of being fixed onto the baseplate of the implant and guiding it towards the intervertebral space, a deployer capable of being inserted in the implant holder tube and including a connection rod capable of enabling actuation of the expansion means.

According to another feature, actuation is performed by fastening the connection rod onto the hooking means of the implant.

According to another feature, the instrumentation comprises at least one charger capable of receiving at least one anchoring device and/or a graft (G), and at least one impacter, the impacter being capable of impacting anchoring devices or delivering graft through the charger.

According to another feature, the instrumentation comprises an implantation pistol including a handle capable of connecting with the implant holder tube via connection means so as to implant at least one implant, an anchoring device and/or a graft towards the vertebra.

According to another feature, the instruments, such as the deployer, the charger or the impacter, may be coupled and uncoupled successively onto and from the pistol during implantation.

According to another feature, the pistol may be connected and disconnected with or without the presence of the instruments, such as the deployer, the charger or the impacter, in the tube of the implant holder.

BRIEF DESCRIPTION OF THE SEVERAL VIEWS OF THE DRAWING

Other features and advantages of the present disclosure will emerge more clearly from the description hereinbelow, given in reference to the appended drawings, in which:

FIGS. 1A and 1B show section views, respectively, along the plane 1A-1A of FIG. 1B, and profile of an intervertebral implant after deployment of the elongated arms according to an embodiment, and FIG. 1C shows a perspective view of the same implant disposed on a vertebra;

FIG. 13A shows a perspective view of an intervertebral implant according to an embodiment after deployment of the elongated arms using instrumentation; and FIGS. 13B and 13C show perspective views of the implant, respectively, before and after loading and deployment of two anchoring devices via the implant using instrumentation;

FIGS. 17A and 17B show perspective views of a vertebral implant according to an embodiment after deployment of the elongated arms, respectively, before and after deployment of two anchoring devices via the implant using instrumentation (in FIG. 16A comprising an implant holder tube of the instrumentation which is shown in section); FIG. 17C shows a perspective view of anchoring devices deployed via the implant;

DETAILED DESCRIPTION OF VARIOUS EMBODIMENTS

Figure 2A:
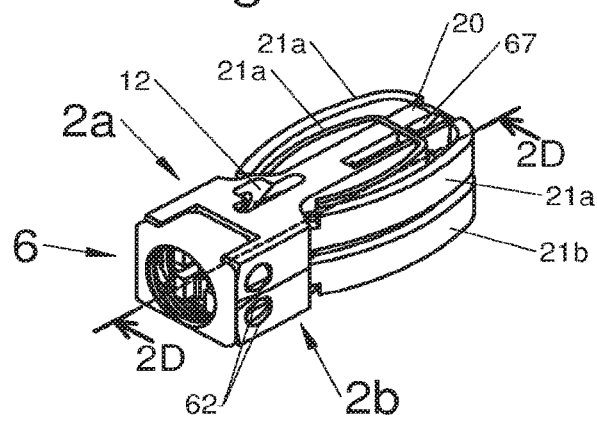
FIGS. 2A and 2B show perspective views of an intervertebral implant according to an embodiment, respectively, before and after lateral deployment of lateral expansion means and deployment of the elongated arms.
Figure 2B:
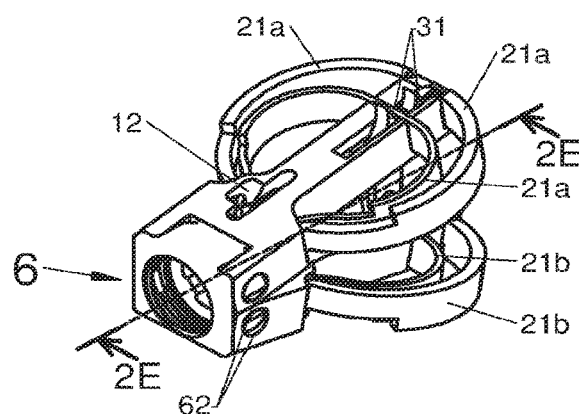
Figure 2C:
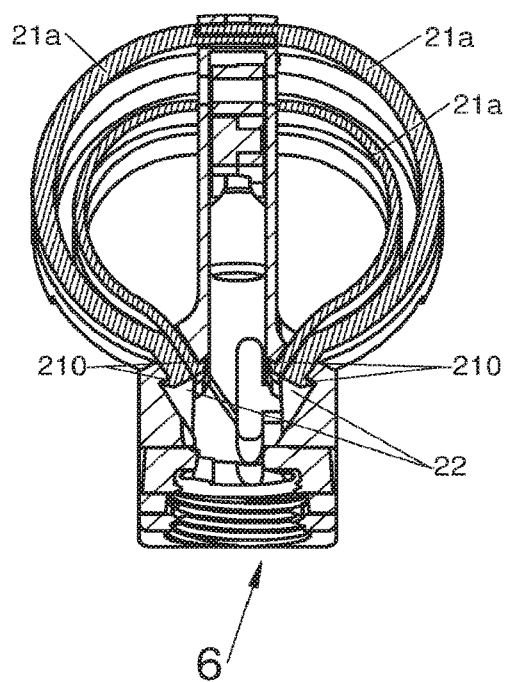
FIG. 2C shows a section view along the plane 2C-2C of FIG. 2E.
Figure 2D:
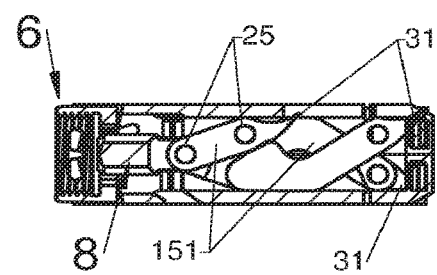
FIGS. 2D and 2E show section views, respectively, along the plane 2D-2D of FIG. 2A and along the plane 2E-2E of FIG. 2B.

The present disclosure relates to a vertebral implant, adapted for use in the spine and intended to be implanted in general in a vertebral segment composed of at least two vertebrae. This implant is provided to be deployed horizontally, vertically and laterally by way of various elements participating in said deployment or expansion of said implant.

These various elements are different from one another, but they have the advantage of all participating in the horizontal, vertical and/or lateral expansion of the implant. This makes it possible to group these elements according to the term "expansion means" and the different technical features of each expansion means will be detailed below. Indeed, this implant could be an implant of "intervertebral" type implanted between two adjacent vertebrae or an implant of "corpectomy" type implanted on a segment which may extend beyond a single intervertebral space, or even over several bodies and/or vertebral spaces. In fact, various embodiments relate to implants fitted with elongated arms and expansion means for reliable, stable and non-invasive implantation so as to propose efficacious arthrodesis (bone fusion) in various implantation sites (different lordosis) and the examples provided hereinabove therefore must not be considered as limiting. In this way, various embodiments could provide an implant which is not designed for the spine but configured (as example in terms of three-dimensional shape) for another type of bone of the locomotor system.

In addition, a person skilled in the art may possibly make use of the two other applications filed on the same day as the present application, by the same applicant, so as to ascertain possible functional and/or structural features which would be insufficiently detailed or not detailed in the present application. In other words, the entirety of these two other applications (description, claims and figures) may therefore be considered, if need be (depending on the applicable law), as being incorporated in the present application by reference.

It will be noted that the designations of the "proximal" and "distal" ends of the implant (1) or of any other element are used in the present application in reference to the direction along which the implant (1) is inserted.

Thus, the wall or the end designated as proximal of the body of the implant is that by which it is generally held to be implanted, whether this wall is really proximal to the implant or not during its implantation.

In the case of spinal implants described in the present application, this proximal end may be effectively disposed towards the rear of the patient or not, as example for the implants which are essentially intended for implantation by posterior or transforaminal route. Consequently, the terms "distal" and "proximal" are not intended to refer simply to the patient or to his anatomical characteristics, but to the direction of insertion of the anchor in the implant and/or of the implant itself (whether this implant is itself implanted along an antero-posterior axis or not).

On the other hand, the terms "vertical" and "horizontal" are generally designated here in a non-limiting manner in reference to the axis of the spine by considering the patient upright and the implant positioned in the spine. On the other hand, the terms "width or lateral" and "length" mean dimensions along a plane perpendicular to the axis of the spine (a transversal plane), with the width being generally in the mediolateral direction whereas the length will be in the antero-posterior direction without this conventional definition having the least limiting implication for various embodiments. In fact, this conventional terminology is to simplify the description of the different technical structures of the present disclosure and cannot therefore have a connotation limited with respect to the real orientation of one of the embodiments. According to certain embodiments, the terms "vertical" or "height" may refer generally to directions or dimensions oriented substantially along the tertiary axis (Z). It will be also noted that the term "substantially" is regularly used in the present description, notably relating to a feature such as an orientation or a direction, so as to indicate that the relevant feature may in fact be slightly different and not be exactly as designated (for example, the expression "substantially perpendicular" should be interpreted as "at least approximately perpendicular" since it may be possible to select an orientation which is not exactly perpendicular to be able to nevertheless fulfill substantially the same function or structural arrangement). Further, terms like the term "substantially" used in the present application may also be interpreted as defining that the technical feature may "in general" ("generally") and often "preferably", as indicated, but that other embodiments or configurations may be within the scope of the present disclosure.

It will be noted that, in the present application, generally the primary (X), secondary (Y) and tertiary (Z) axes are substantially orthogonal to one another, the primary axis (X) corresponding to the direction along which the implant will be displaced during its implantation in the patient, as shown for example in FIG. 1C. In addition, in general the references in the present application will consider that the primary axis is a horizontal axis, the secondary axis (Y) is a lateral axis and the tertiary axis (Z) is a vertical axis. For example in certain embodiments, the intervertebral implant (1) comprises a body (20) extending longitudinally along a primary axis (X), between a proximal end and a distal end. Generally, in the present application, the distal end may be the end by which the implant is introduced to the intervertebral space and the proximal end is the end by which the implant is held during its implantation.

In certain embodiments, the implant (1) comprises a baseplate (6) disposed at the proximal end and by which the implant (1) is gripped by instrumentation adapted to be implanted in the intervertebral space. The baseplate thus comprises, on its proximal end, complementary attachment means, such as for example and without limitation an internal thread, with instrumentation (for example an implant holder tube (PI)), as shown for example in FIGS. 1A, 2A to 2E, 3A to 3E, 4A to 4C, 8A to 8D, 14E, 15C, 16C, 16D and 17D, to facilitate handling during gripping of the implant by the instrumentation for the implantation or the removal of said implant. In certain embodiments, said attachment means of the baseplate are complementary to attachment means (34) of an insert (3) which can, without limitation, be threads, as shown for example in FIGS. 5A to 5F, 6A to 6E, 7A to 7C, 7E and 7F, allowing the insert to be easily guided in the deployment of the implant (1).

The implant (1) further comprises a plurality of elongated arms (2a, 2b, 2c, 2d) along the primary axis (X) and each including at least one vertebral support surface (4a, 4c), the arms (2a, 2b, 2c, 2d) being articulated at least on the baseplate (6) such that the implant comprises on the one hand a folded-back position in which the arms (2a, 2b, 2c, 2d) are close to each other, and on the other hand a deployed position in which the arms (2a, 2b, 2c, 2d) are moved away from each other along at least one secondary axis (Y) and/or at least one tertiary axis (Z). Indeed, the implant (1) comprises at least two elongated arms (2a, 2b), as shown for example in FIGS. 1A to 1C, 2A to 2E, 3A to 3E, 4A to 4D, 8A to 8E, 11A to 11C, 12A to 12C, 13A to 13C, 14E, 15A to 15C, 16A to 16D and 17A to 17C, disposed on each other and symmetrically along the body (20) so as to implement a translation movement along the secondary axis (Y) and/or the tertiary axis (Z) between said folded-back position and said deployed position. As per another embodiment, the implant (1) comprises at least four elongated arms (2a, 2b, 2c, 2d), as shown for example in FIGS. 5A, to 5F, 6A to 6E, 7A to 7D, 7F, 9A to 9C and 10A to 10F, also disposed symmetrically along the body (20) of the implant (1) so as to describe a translation movement along the secondary axis (Y) and/or the tertiary axis (Z) between said folded-back and deployed positions. It is evident that the primary (X), secondary (Y) and tertiary (Z) axes are substantially orthogonal to each other. In this way, the arms (2a, 2b, 2c, 2d) of the implant (1) according to various embodiments are capable of being deployed vertically and/or laterally so as to provide a larger surface for absorbing the entire load distribution, better stability and increased resistance to subsidence in the vertebrae. In general, the implant (1) is implanted with the arms (2a, 2b, 2c, 2d) in folded-back position in the intervertebral space so as to minimize the dimensions of the implant (1) and produce the least invasive implantation possible for the patient. Then, the arms are deployed vertically or in height along the tertiary axis (Z) and/or laterally or in width along the secondary axis (Y) using the expansion means (3, 8, 21, 21a, 21b, 22, 25, 66, 67, 69, 151) of the implant (1) to reinforce the stability of the implant and so that the implant occupies a larger space between the vertebrae so as to make bone fusion easier and more reliable. It will be noted that, according to one of the embodiments, the expansion means may be either achieved by an insert (3), a hooking means (8), pivot arms (21, 21a, 21b), a pivoting axis (25), guide means (66, 67), a separating element (69) and/or pivoting branches (151). It will be noted that, preferably, initially the arms are deployed horizontally along the primary axis (X), then secondly, the arms are deployed vertically along the tertiary axis (Z) and/or laterally along the secondary axis (Y). This configuration has the advantage of limiting the force exerted on the vertebrae by the arms during their deployment in the intervertebral space.

In certain embodiments, at least one of the upper and/or lower surfaces (4a, 4c) of the arms (2a, 2b, 2c, 2d) of the body (20) includes notches, for example as shown in most of the figures (for example FIG. 5A to 5C, 10A to 10D or 14E), to avoid shifting of the implant (1) between the vertebrae between which it is intended to be implanted before bone fusion is sufficient. Also, in various embodiments, the body (20) and/or the arms (2a, 2b, 2c, 2d) includes at least one part beveled and/or chamfered on at least one peripheral portion of at least one of its upper and lower surfaces of the distal end, so as to facilitate insertion of the implant (1) between the vertebrae (V), for example as shown in most of the figures (for example FIG. 2A to 2C, 5A to 5C, 11A to 11D or 17C).

Also, the implant (1) comprises expansion means (3, 8, 25, 21, 21a, 21b, 22, 66, 67, 69, 151) for expansion of the arms (2a, 2b, 2c, 2d) of the body (20) of said implant (1) between the folded-back and deployed positions.

These expansion means comprise on the one hand expansion means in height (3, 8, 25, 66, 67, 69, 151), and/or on the other hand expansion means in width (3, 21, 21a, 21b, 22, 151) for deployment of the arms (2a, 2b, 2c, 2d) such that the implant occupies a larger space and enables increased stability and reliability of the implantation between the intervertebral space.

Figure 18A:
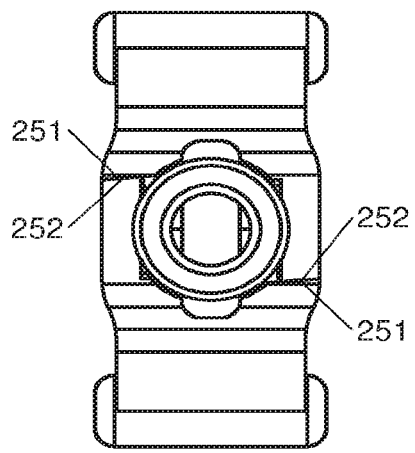
FIGS. 18A and 18B show perspective views of the expansion means according to an embodiment, respectively, after and before assembly of said means.
Figure 18B:
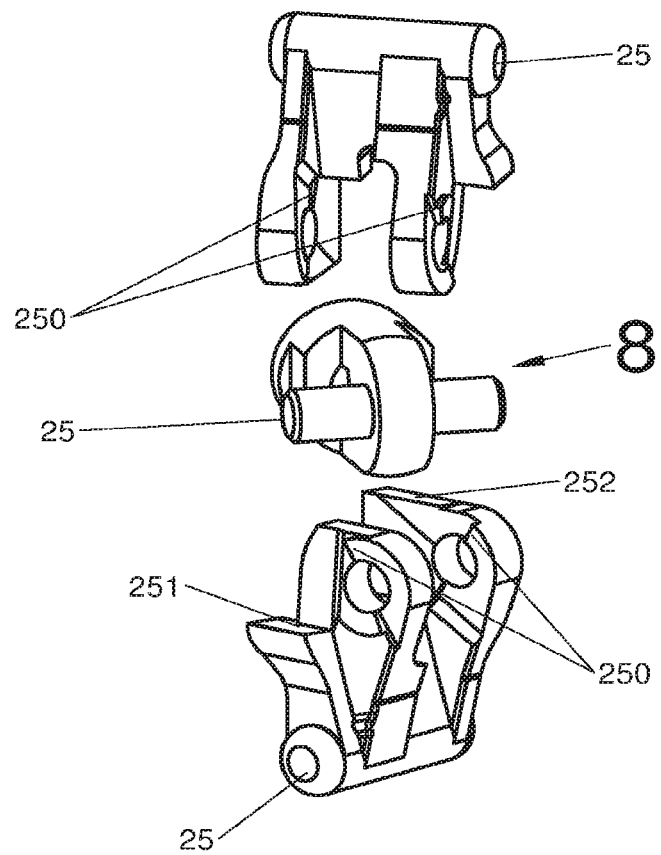
Figure 19A:
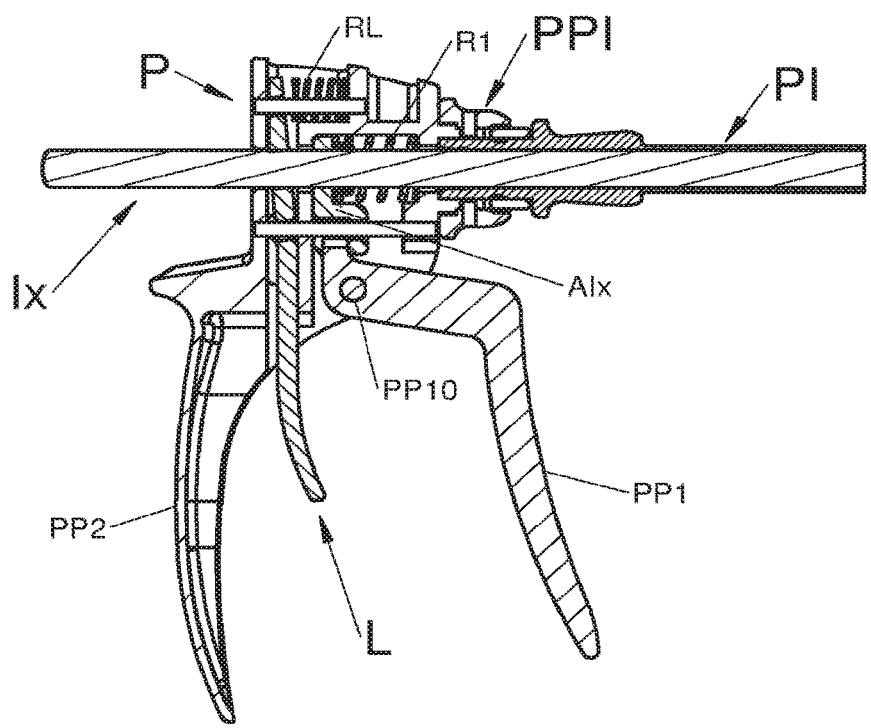
FIGS. 19B and 19A shows views, respectively, in perspective and section along a median plane of FIG. 19B of an implantation pistol according to an embodiment.
Figure 19B:
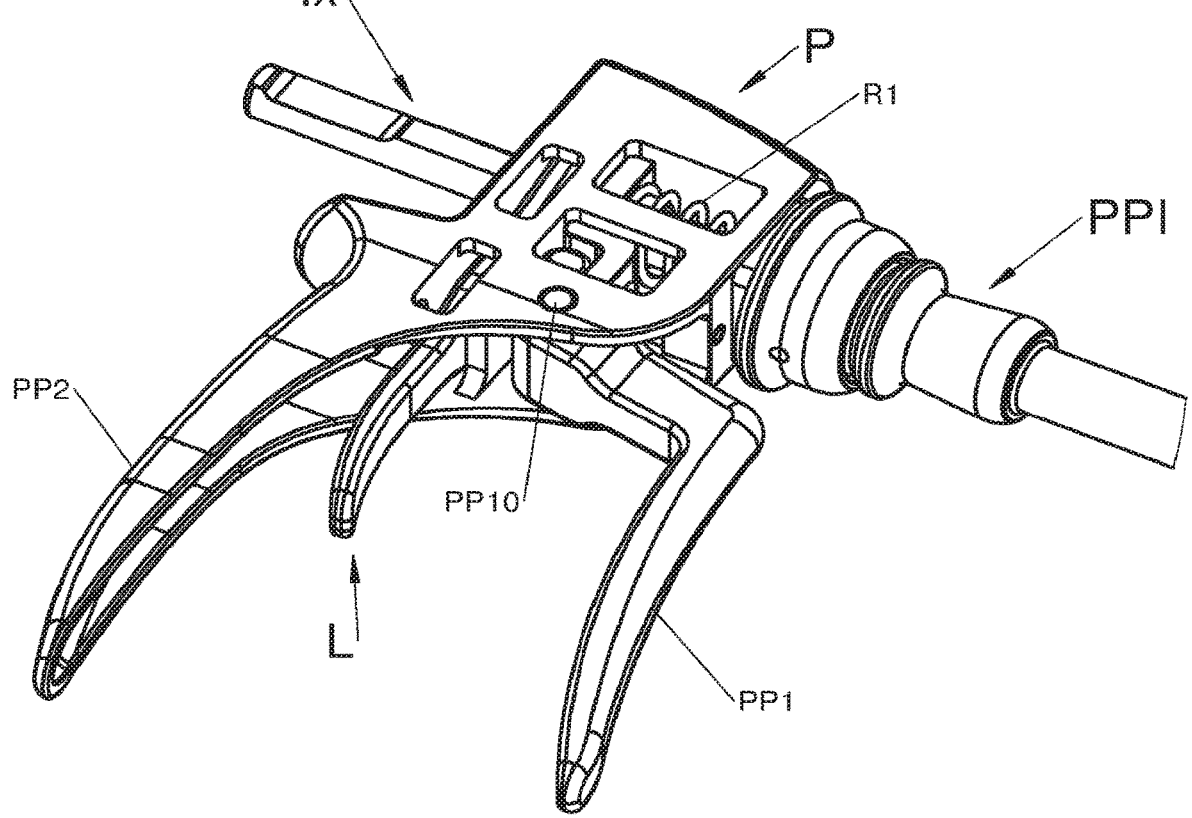
Figure 20A:
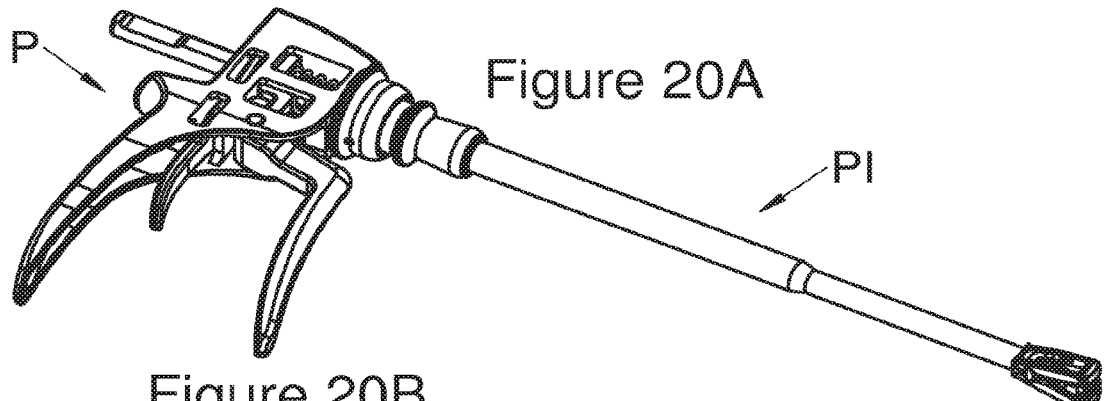
FIGS. 20A and 20E show perspective views of the implantation pistol, respectively, before and during disengagement of the instrumentation for implantation of an implant.
Figure 20B:
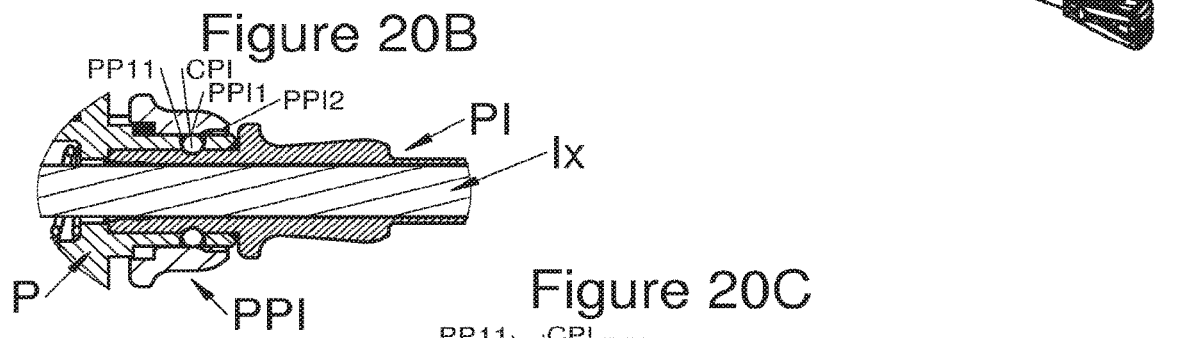
FIGS. 20B, 20C and 20D show section views along a median plane of the pistol, respectively, before and during the disengagement of the instrumentation.
Figure 20C:
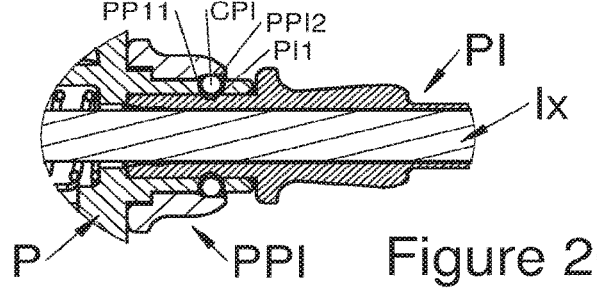
Figure 20D:
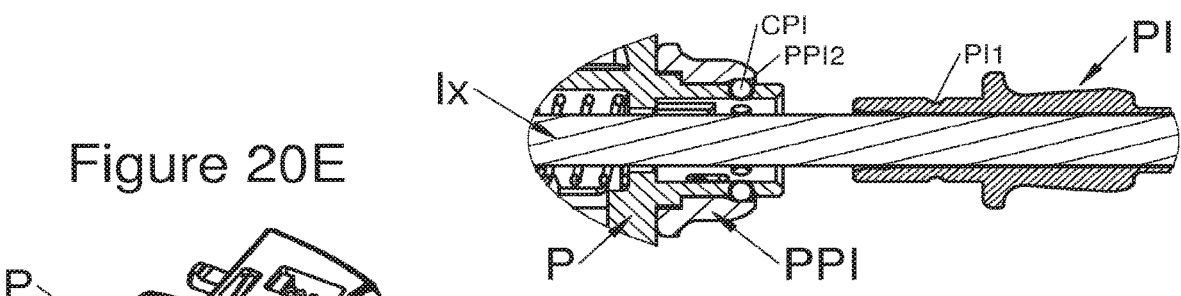
Figure 20E:
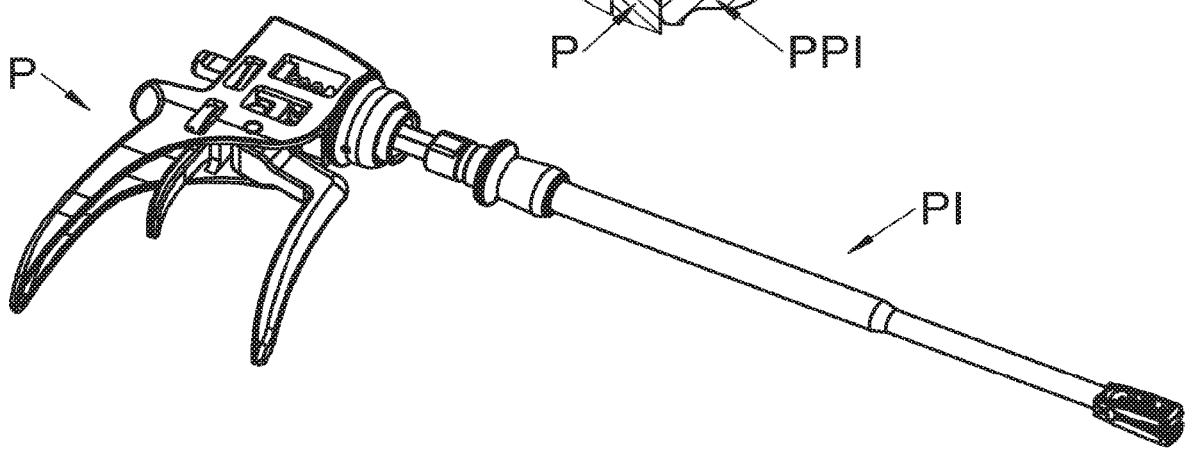

In certain embodiments, the expansion means in height (3, 8, 25, 66, 67, 69, 151) comprise at least two branches (151) pivotably mounted one relative to the other and attached to the elongated arms (2a, 2b, 2c, 2d) by at least guide means (66, 67) such that translation of the expansion means parallel to the primary axis (X) causes pivoting of the branches (151) one relative to the other and moves the arms (2a, 2b, 2c, 2d) away from each other, along the secondary axis (Y) and/or the tertiary axis (Z). In certain embodiments, pivoting of the branches (151) one relative to the other occurs around a pivoting axis (25) substantially oriented parallel to the tertiary axis (Z) to move the elongated arms (2a, 2b, 2c, 2d) away along this axis and enable expansion in height of the implant (1). In this way, one of the two branches (151) comprises on the one hand a first end (152) fastened to a distal end of at least one of the arms (2a, 2b, 2c, 2d), for example and non-limiting by clipping (FIG. 14C), and on the other hand a second end fastened to the other branch (151) via the pivoting axis (25) by locking means (250) such as, without limitation, complementary spurs (250) and/or abutments (251,252) between said branches (FIGS. 18A and 18B). In certain embodiments, this configuration of the branches (151), as shown for example in FIGS. 14A, 14C, 18A and 18B, lets the branches (151) be pivotably mounted one relative to the other, by way of the pivoting axis (25), and fastened to the arms (2a, 2b, 2c, 2d) stably such that the translation movement of the branches causes deployment of the arms (2a, 2b, 2c, 2d) along the secondary axis (Y) and/or the tertiary axis (Z). In certain embodiments, the branches (151) enable expansion in height and/or in width of the arms (2a, 2b, 2c, 2d) of the implant (1), are disposed at the distal end of the body (20) of the implant. Said branches comprise at least one projecting portion (31) capable of anchoring itself in at least one vertebra (V) after deployment of the arms (2a, 2b, 2c, 2d) in the intervertebral space, such as for example teeth (31) or any other means for anchoring of the deployed arms in the vertebrae. For example, in the embodiment of FIG. 2E, the branches (151) comprise teeth (31) on their lower and upper ends, which facilitate the stable anchorage of the deployed arms in height and/or in the width of the implant (1) in the vertebrae (V).

In certain embodiments, the implant (1) comprises guide means (66, 67) comprising inner surfaces (67) of the arms (2a, 2b, 2c, 2d) which are non-parallel to each other and divergent in the direction of the distal end such that the arms (2a, 2b, 2c, 2d) are moved away from each other along the tertiary axis (Z) during translation of the expansion means along the primary axis (X). Indeed, the guide means (66, 67) comprise at least one projection (66) disposed on at least one of the expansion means, for example and without limitation the insert (3) as shown for example in FIGS. 5E and 6E, and at least one groove (67) disposed on at least one of the elongated arms (2a, 2b, 2c, 2d), such that the projection (66) cooperates with the groove (67) when said expansion means is shifted along the body (20) during deployment of the elongated arms (2a, 2b, 2c, 2d). In this way, displacement along the primary axis (X) of the projection (66) in the groove (67), as shown for example in FIGS. 5A to 5E, 6A to 6E, 7A to 7F and 10F, enables expansion in height or vertical deployment of the elongated arms of the implant along the tertiary axis (Z).

Figure 6A:
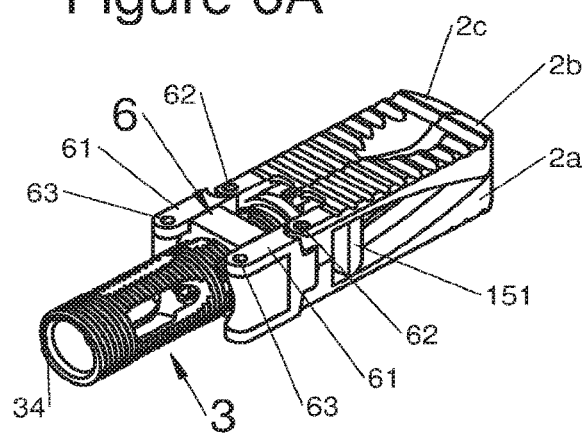
FIGS. 6A, 6B and 6C show perspective views of an intervertebral implant according to an embodiment, respectively, before, during and after insertion of an insert and deployment of the elongated arms.
Figure 6B:
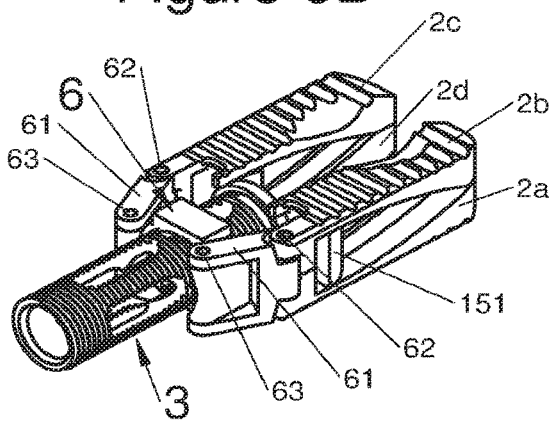
Figure 6C:
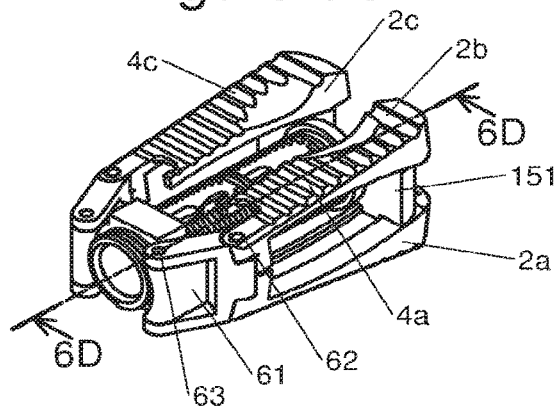
Figure 6D:
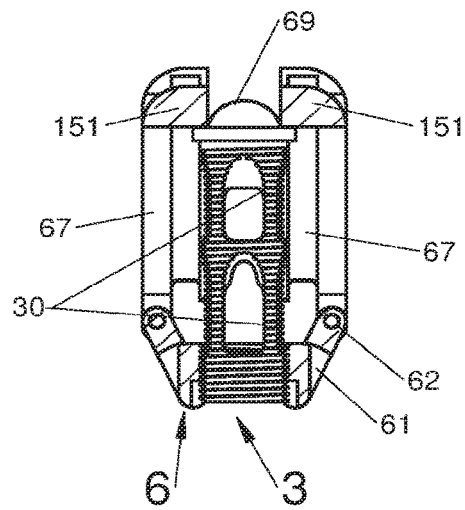
FIG. 6D shows a section view along the plane 6D-6D of FIG. 6C.
Figure 6E:
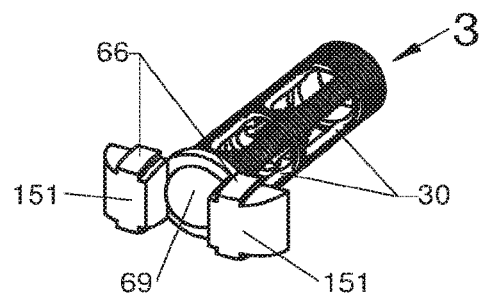
FIG. 6E shows a perspective view of the insert and expansion means of the implant.
Figure 7A:
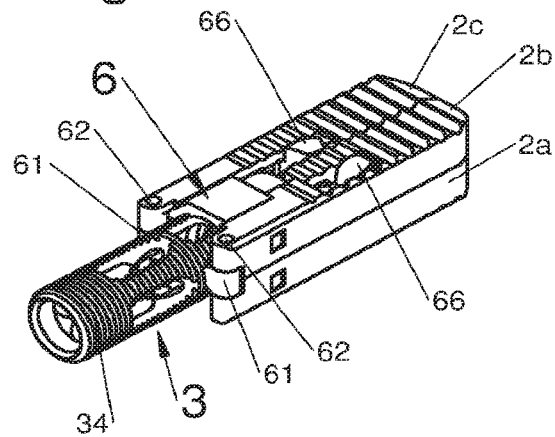
FIGS. 7A, 7B and 7C show perspective views of an intervertebral implant according to an embodiment, respectively, before, during and after insertion of an insert and deployment of the elongated arms.
Figure 7B:
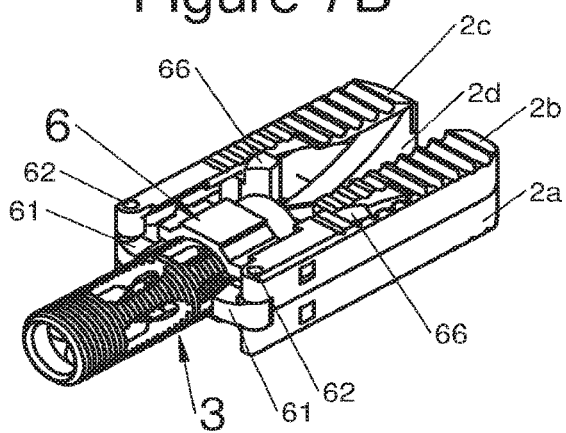
Figure 7C:
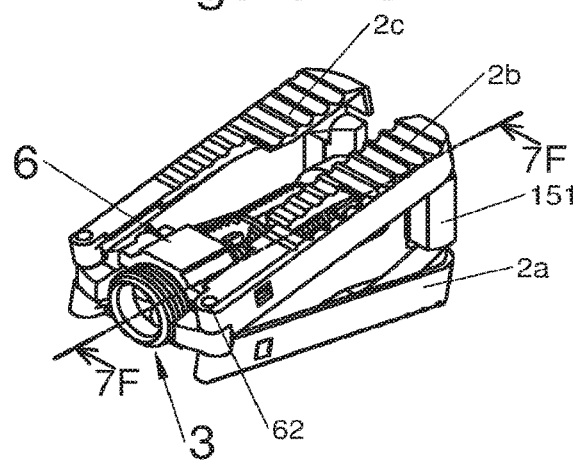
Figure 7D:
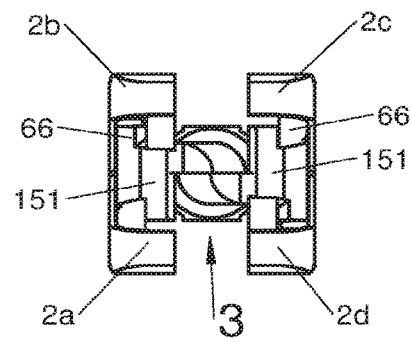
FIGS. 7D and 7F show views, respectively, of the front/distal and sectional face along the plane 7F-7F of FIG. 7C.
Figure 7E:
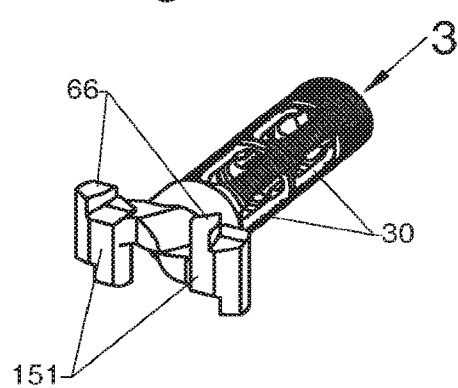
FIG. 7E shows a perspective view of the insert and expansion means of the implant.
Figure 7F:
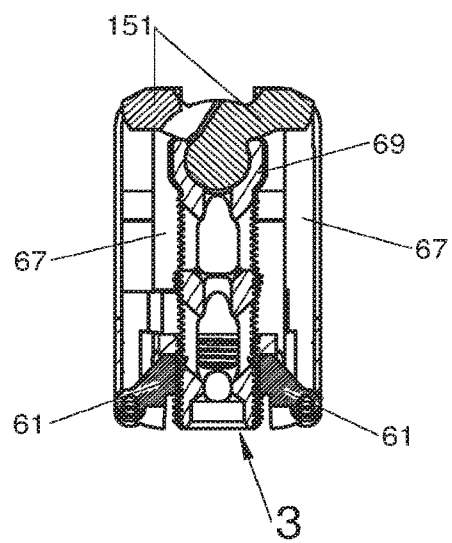
Figure 8A:
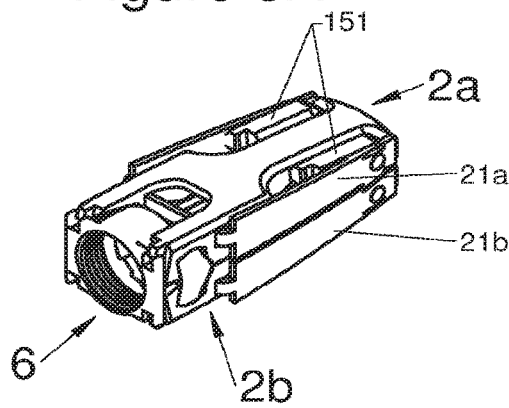
FIG. 8A shows a perspective view of an intervertebral implant according to an embodiment prior to lateral deployment of lateral expansion means.
Figure 8B:
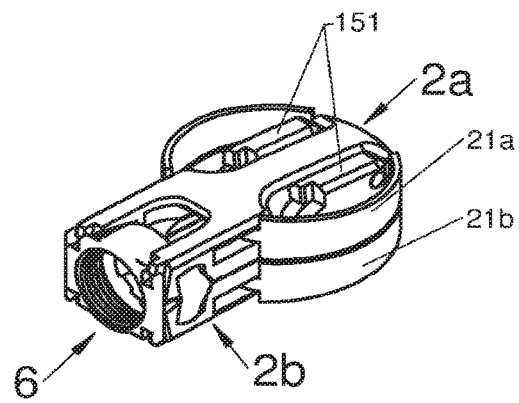
FIGS. 8B and 8C show perspective views of an intervertebral implant after lateral deployment of lateral expansion means and comprising elongated arms, respectively, in folded-back position and in deployed position.
Figure 8C:
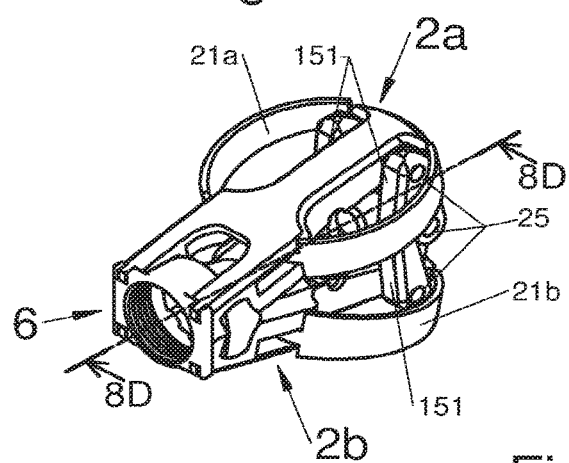
Figure 8D:
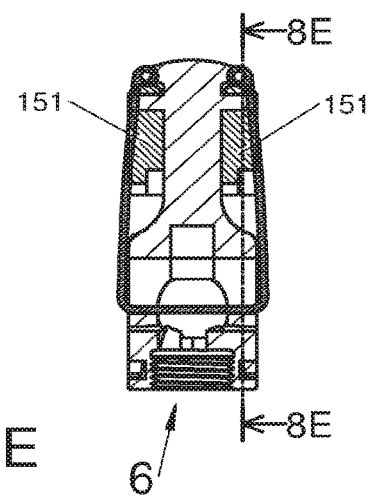
FIGS. 8D and 8E show section views, respectively, along the plane 8D-8D of FIG. 8C, and along the plane 8E-8E of FIG. 8D.
Figure 8E:
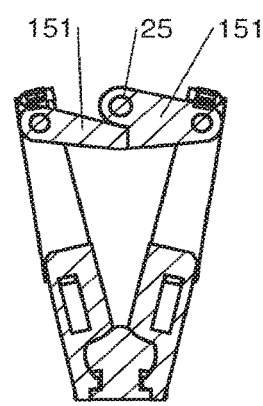
Figure 9A:
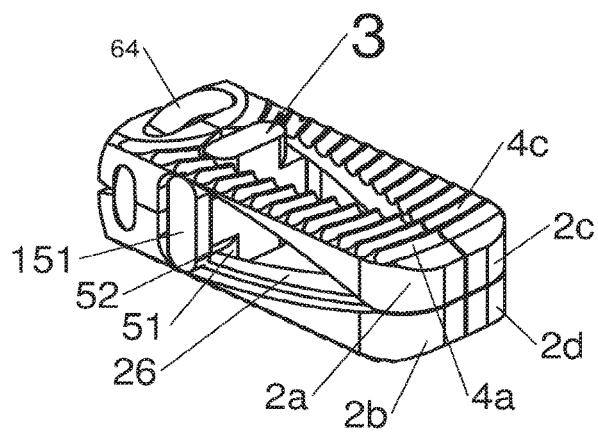
FIGS. 9A, 9B and 9C show perspective views of a vertebral implant according to an embodiment, respectively, before, during and after insertion of an insert and deployment of the elongated arms.
Figure 9B:
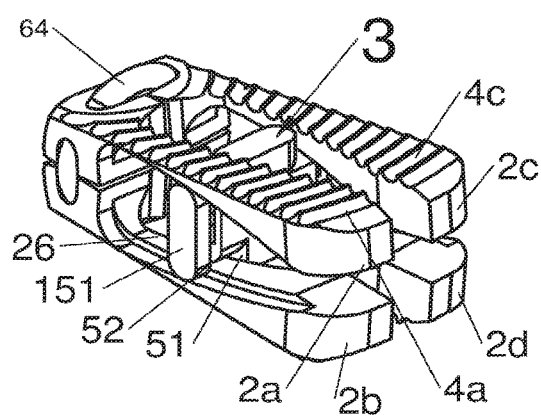
Figure 9C:
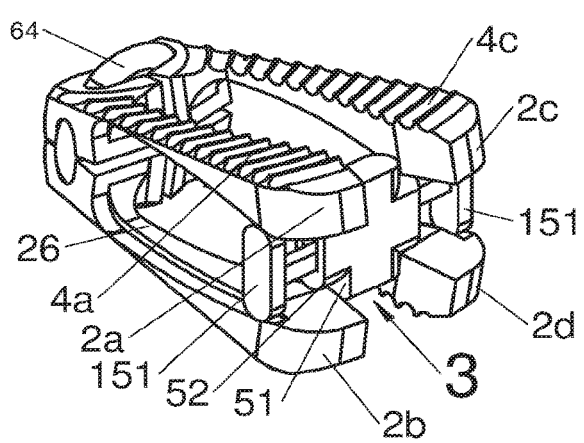
Figure 9D:
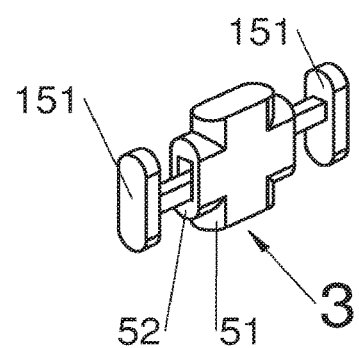
FIG. 9D shows a perspective view of the deployed insert.

In certain embodiments, the implant (1) comprises at least one separating element (69) disposed on at least one of the expansion means, for example and without limitation the insert (3) as shown for example in FIGS. 6D, 6E and 7F. Said separating element (69) being able to be a projecting portion (69), as shown for example in FIG. 6D, or a hollow portion (69) complementary to a rounded surface of the branches (151), as shown for example in FIG. 7F. For example, in the embodiment of FIGS. 6A to 6E, said separating element (69) disposed on the distal end of the insert (3) and having a projecting portion (which may be spherical or non-spherical) allows the branches (151) to be separated to trigger the deployment of the elongated arms (2a, 2b, 2c, 2d) along the secondary (Y) and tertiary (Z) axes when the insert (3) is displaced longitudinally along the primary axis (X). For example, in the embodiment of FIGS. 7A to 7F, the hollow portion of said separating element (69) of the insert (3), cooperates with the rounded surface of the branches (151) to enable both the separation of said branches and the deployment of the elongated arms (2a, 2b, 2c, 2d) along the secondary (Y) and tertiary (Z) axes, when the insert (3) is displaced longitudinally along the primary axis (X).

In certain embodiments, the expansion means (3, 8, 25, 21, 21a, 21b, 22, 66, 67, 69, 151) of the implant also comprise expansion means in width (22, 21, 21a, 21b) of the implant, along at least one direction generally parallel to the secondary axis (Y). For example, in various embodiments, these expansion means in width (22, 21, 21a, 21b) of the implant comprise blades (21) secured to the distal end of the arms (2a, 2b) of the implant and rotatably mounted relative to the rest of the arms (2a, 2b). In certain embodiments, the blades (21) may be flexible or rigid and may be connected to the expansion means in height, such that the translation of an actuator may cause the rotation of the blades (21), and associated expansion of the width covered by the implant. As shown for example in FIG. 1A, the implant (1) may be implanted with the elongated arms in the folded-back or closed position then the blades (21) are deployed laterally by an actuator using a traction or pressure exerted by the surgeon to cover as much of the surface as possible in the intervertebral space. For example, in the embodiment of FIGS. 1A to 1C, the actuator may be implemented in the form of a bar (5), which may deploy the blades (21) by translation of traction of the bar (5), but other similar embodiments may use the translation by pressure on the bar (5) to deploy the blades (21).

In various embodiments, the expansion means in width (22, 21, 21a, 21b) of the implant comprise pivot arms (21a, 21b) pivotably mounted on a pivoting axis (22) and with respect to the body (20) between the folded-back or closed position in which the pivot arms (21a, 21b) may border the body (20), and the deployed position in which the arms (21a, 21b) are moved away from the body (20) in an expansion configuration, for example, generally along the secondary axis (Y). In certain embodiments, the pivoting axis (22) and the pivoting blades (21a, 21b) may be configured in such a manner that the pivoting blades (21a, 21b) may be substantially parallel to the pivoting axis (22) in the insertion configuration and not parallel to the pivoting axis (22) in the deployed configuration. In certain embodiments, as shown for example in FIGS. 2A to 2E, 3A to 3C, 4A to 4C and 8A to 8C, the pivot arms (21a, 21b) increase the final surface occupied by the implant between the intervertebral space. In certain embodiments, the pivot arms (21a, 21b) deployed laterally form cavities along the body (20) of the implant (1), which will facilitate and reinforce bone fusion via said cavities et may provide a space for bone tissue (or substitute) grafts.

In certain embodiments, pivoting of the branches (151) one relative to the other, which occurs around the pivoting axis (25) oriented substantially parallel to the tertiary axis(Z) to move away the elongated arms (2a, 2b, 2c, 2d) along the secondary (Y) and tertiary (Z) axes, for expansion of the implant in width. For example, as shown in FIG. 5A to 5C, 6A to 6C or 7A to 7C, the lateral deployment of the arms (2a, 2b, 2c, 2d) is performed by way of shifting of the insert (3) along the body (20) of the implant (1).

In certain embodiments, a portion of the distal end (210) of the arm (21) slides along the body when the implant is in the deployed position (i.e., the final use position). The arm (21) then deploys along a secondary axis (Y) substantially perpendicular to the body, so as to become bent. Thus, the deployment of the arm (21) allows the implant to occupy a greater space, while allowing greater stability and reliability because the surface area, in contact with the bone of the vertebrae, as example to cortical bone, is greater. In other words, the implant has increased its volume due to the sliding of a portion of the distal end of the arm. This is not a redistribution of the initial volume of the implant, but in fact an increase thereof.

In certain embodiments, expansion means (3, 8, 25, 66, 67, 69, 151) in height may comprise an insert (3) having branches (151) pivoting around a pivoting axis (25) and guide means (66, 67) comprising the guide surface (66) cooperating with grooves (67), which may have a constant depth or a variable depth. In certain embodiments, expansion means in width (3, 21, 21a, 21b, 22, 151) may comprise an insert (3) equipped with branches (151) pivoting around a pivoting axis (25) (illustrated for example in FIGS. 5A to 5E) and/or sliding with respect to a separating element (69) (illustrated as spherical for example in FIGS. 6A to 6E, but replaceable by other convex shapes), wherein the guide means (66, 67) may comprise a guide surface (66) cooperating with grooves (67) the depth whereof decreases in the direction of the distal end of the body of the implant.

In certain embodiments, in which the expansion means comprise a groove (67) having a depth which diminishes toward the distal end of the body of the implant, which may enable a portion or the totality of the extension in height of the arm (2a, 2b, 2c, 2d). It will be noted that, preferably, the arms are first deployed laterally along the secondary axis (Y) and then vertically along the tertiary axis (Z), for example as shown in FIG. 5A to 5C, 6A to 6C or 8A to 8C.

In certain embodiments, the expansion means therefore comprise at least one insert (3) which may be screwed through the baseplate (6) to cause translation of a portion or of the totality of the expansion means (3, 8, 21, 21a, 21b, 22, 25, 66, 67, 69, 151) relative to the body (20) of the implant during deployment of the elongated arms. For example, as described hereinabove, displacement of the insert (3) along the primary axis (X) and along the body (20) of the implant may deploy the arms (2a, 2b, 2c, 2d) along the secondary axis (Y) and/or the tertiary axis (Z). In certain embodiments, the insert (3) may guide an expansion in height of the implant by a vertical displacement of the elongated arms (2a, 2b, 2c, 2d) along the tertiary axis (Z), as shown for example in FIG. 5A to 5C, 6A to 6C or 7A to 7C. In certain embodiments, the insert (3) may guide an expansion in width of the implant by a lateral displacement of the elongated arms (2a, 2b, 2c, 2d) along the secondary axis (Y), as shown for example in FIG. 5A to 5C, 6A to 6C or 7A to 7C. In certain embodiments, the insert (3) may be provided with branches (151) which may be separated from one another by a separating element (69) for translation of the expansion means with respect to the body of the implant during the deployment of the elongated arms. In certain embodiments, said separating element (69) disposed on the distal end of the insert (3) may be used to exert pressure on the branches (151) to separate them from one another so as to obtain lateral expansion of said arms (2a, 2b, 2c, 2d) of the implant. For example, in the embodiment in FIGS. 9A to 9D, the insert (3) comprises lateral extensions (151) which deploy laterally when the insert is moved along the body (20). In this configuration, the insert comprises two guide surfaces (51, 52) with at least one inner and lateral wall (26) of the body (20) of the implant (1) enabling horizontal and lateral displacement of the insert (3) along the body (20) as shown for example in FIGS. 9A to 9C. Depending on the arrangement and the shape of the insert following a particular implantation, the structures as described above may allow either successive expansion of the implant along the primary axis (X), the secondary axis (Y) and/or the tertiary axis (Z), or expansion of the implant simultaneously along one of the combinations of the three orthogonal axes (X, Y, Z). For example in FIGS. 9A to 9C, the simultaneous reduction of the guide surface along the secondary axis (Y) and the tertiary axis (Z) toward the distal end of the implant, implements simultaneously the expansion, respectively along the axes.

Figure 5A:
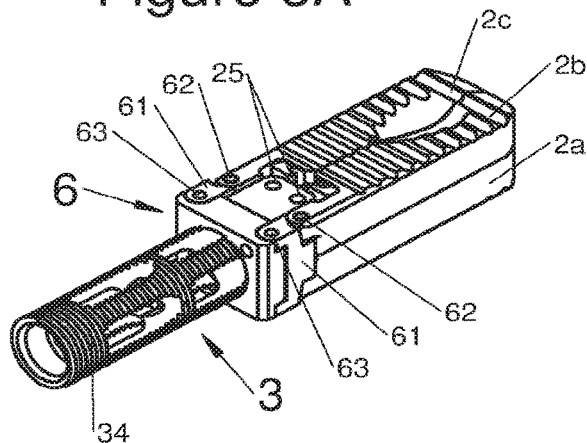
FIGS. 5A, 5B and 5C show perspective views of an intervertebral implant according to an embodiment, respectively, before, during and after insertion of an insert and deployment of the elongated arms.
Figure 5B:
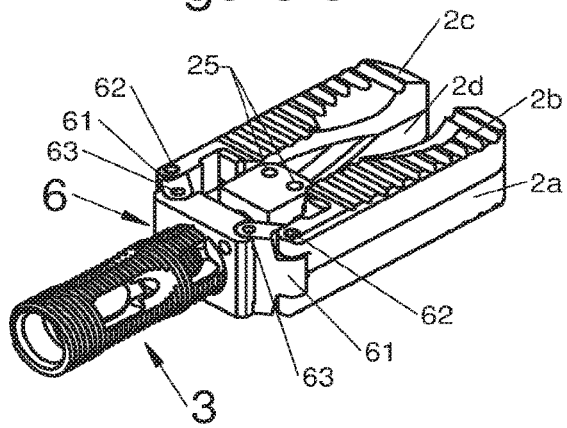
Figure 5C:
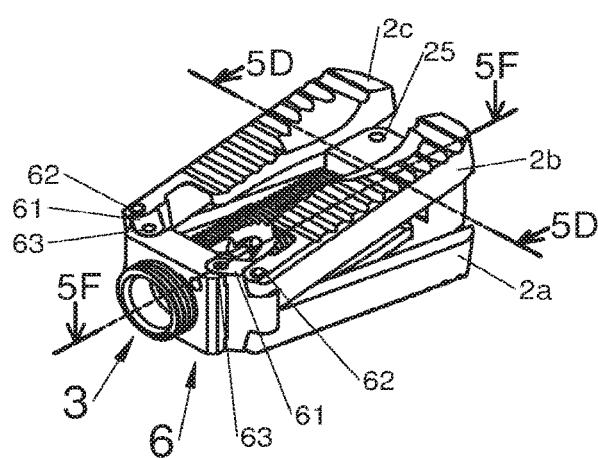
Figure 5D:
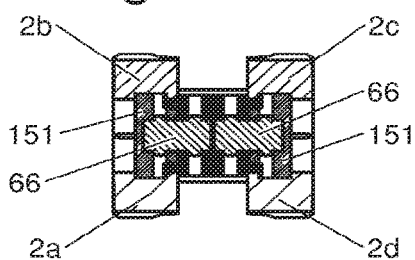
FIGS. 5D and 5F show views, respectively, of the front/distal and sectional face along the plane 5F-5F of FIG. 5C.
Figure 5E:
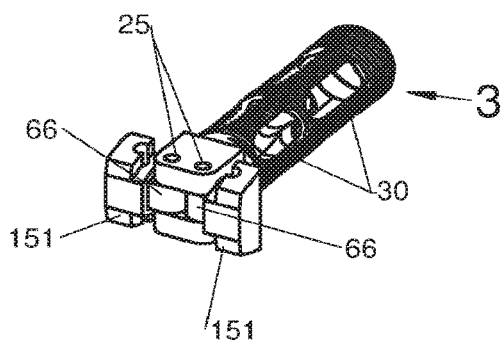
FIG. 5E shows a perspective view of the insert and expansion means of the implant.
Figure 5F:
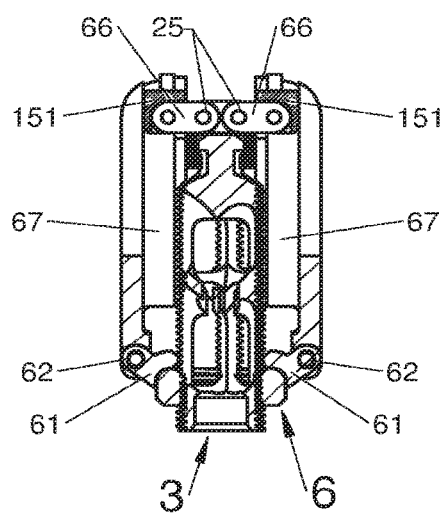

In certain embodiments, the insert (3) may be a cylindrical tube, as shown for example in FIG. 5E or 6E, threaded and comprising cavities (30) to allow bone fusion via said cavities.

Figure 12A:
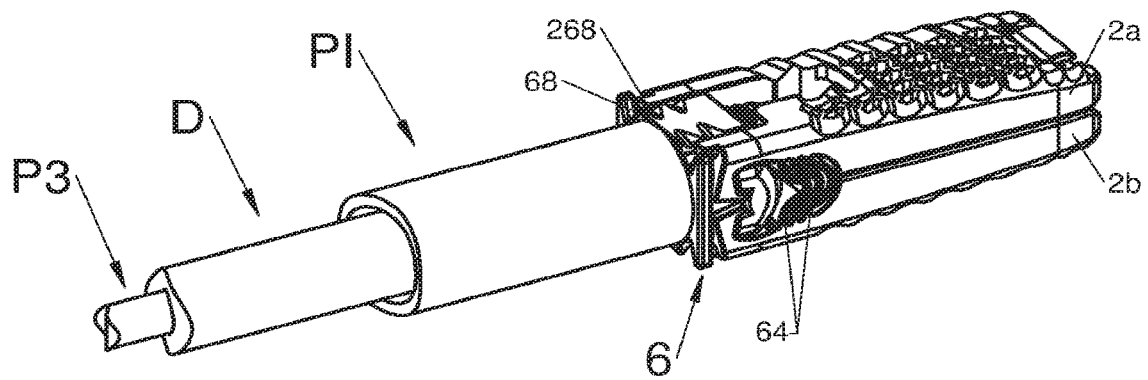
FIGS. 12A and 12B show perspective view of an intervertebral implant according to an embodiment, respectively, before and during deployment of expansion means and elongated arms using instrumentation.
Figure 12B:
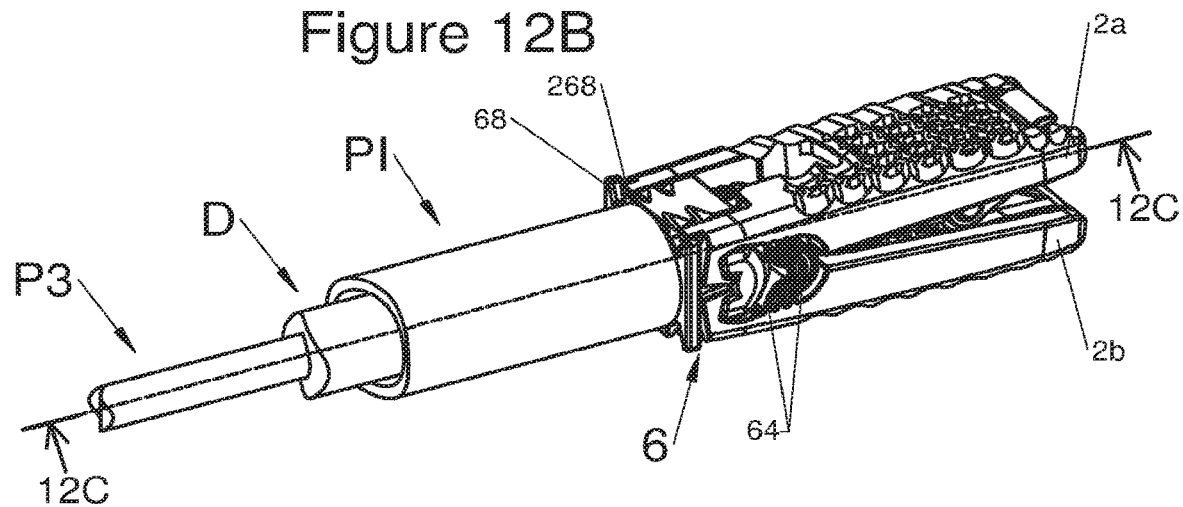
Figure 12C:
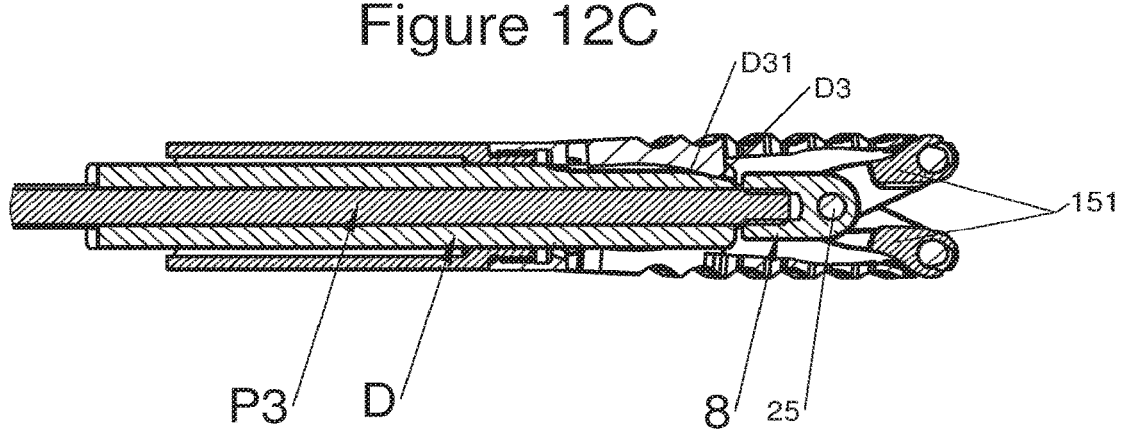
FIG. 12C shows a section view along the plane 12C-12C of FIG. 12B.

In certain embodiments, the insert (3) may be screwed through the baseplate to a hooking means (8) by instrumentation (for example a connection rod (P3)), as shown for example in FIG. 12C. In certain embodiments, the expansion means comprise at least one hooking means (8) with at least one instrumentation (PI, P3, D, D30, D31) which may be fixed to the branches (151) so as to cause translation of the expansion means relative to the body (20) of the implant (1) during deployment of the elongated arms (2a, 2b, 2c, 2d). In certain embodiments, the insert (3) screwed to the hooking means (8) by the connection rod (P3) of the instrumentation may allow, on the one hand the deployment of the arms (2a, 2b, 2c, 2d) of the implant (1) during its implantation in the intervertebral space, and on the other hand, the folding of the arms (2a, 2b, 2c, 2d) of said implant (1) during its withdrawal from the intervertebral space.

In certain embodiments, the elongated arms (2a, 2b, 2c, 2d) may be articulated at least partially on the baseplate (6) between said folded-back or closed and deployed positions. Par example, the baseplate (6) may comprise an articulation (64) capable of joining the arms (2a, 2b, 2c, 2d) together on the proximal end of the body (20). In fact, as shown for example in FIGS. 9A, 11C and 12A, an articulation (64) is disposed between the elongated arms (2a, 2b, 2c, 2d) and the baseplate (6) and oriented parallel to the tertiary axis (Z) and/or to the secondary axis (Y) to move away said arms along this axis or these axes and enable expansion in height and/or in width of the implant (1). Due to this, as shown for example in FIGS. 9A to 9C, the articulation (64) may form a ring segment allowing the implant (1) to create expansion in height and in width which may be simultaneous or sequential. In certain embodiments, the implant (1) comprises other articulations (61, 62, 63) capable of articulating the baseplate (6) and the elongated arms (2a, 2b, 2c, 2d) between the folded-back position and the deployed position. In fact, these articulations (61, 62, 63) form reciprocal coupling means (62, 63) between the baseplate (6) and at least one of the elongated arms (2a, 2b, 2c, 2d). As shown for example in FIGS. 1B, 2A, 2B, the baseplate (6) and the arms (2a, 2b, 2c, 2d) are connected together by at least one coupling means (62) for articulating them between said folded-back and deployed positions and producing expansion in height of the implant. On the other hand, the articulations (61, 62, 63) comprise at least one plate (61) capable of being fixed between the baseplate (6) and the proximal end of at least one elongated arm (2a, 2b, 2c, 2d) such that the plate (61) is articulated at the same time on the baseplate (6) and on the proximal end of the arms (2a, 2b, 2c, 2d) In fact, these articulations (61, 62, 63) also form reciprocal coupling means (62, 63), on the one hand, between the plate (61) and the baseplate (6), and on the other hand, between the plate (61) and the proximal end of at least one of the elongated arms (2a, 2b, 2c, 2d). In this way, as shown for example in FIGS. 5C, 6C, 7C, 10C, the plate (61) is joined to the baseplate (6) by at least one coupling means (63) and to at least one of the arms (2a, 2b, 2c, 2d) by at least one coupling means (62), allowing articulation of the baseplate with the arms between said folded-back and deployed positions and producing expansion in height and/or in width of the implant (1). Said coupling means comprise, for example and without limitation, pins, hooks, rings and any other means allowing the baseplate to be linked to the elongated arms of the implant.

Figure 2E:
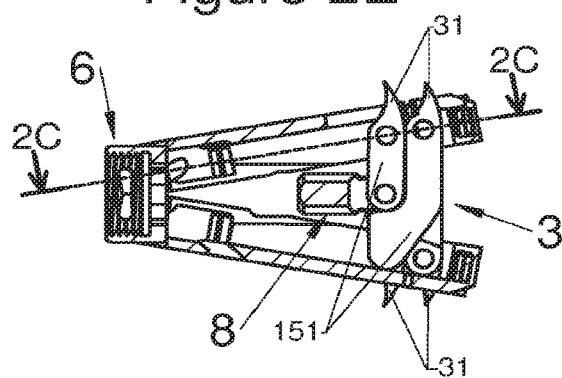
Figure 3A:
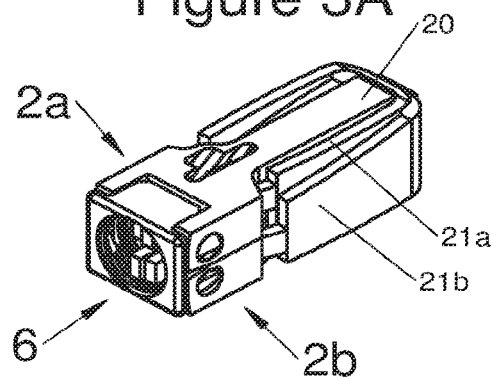
FIG. 3A shows a perspective view of an intervertebral implant according to an embodiment prior to lateral deployment of lateral expansion means.
Figure 3B:
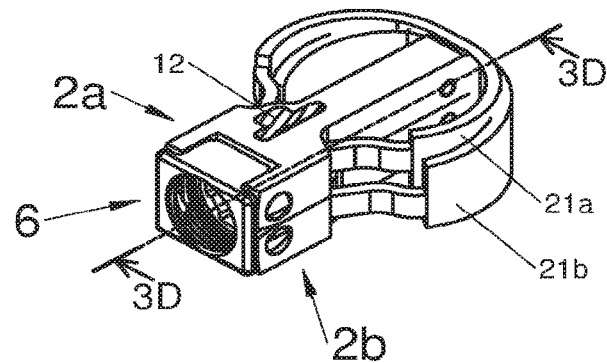
FIGS. 3B and 3C show perspective views of an intervertebral implant after lateral deployment of lateral expansion means and comprising elongated arms, respectively, in folded-back position and in deployed position.
Figure 3C:
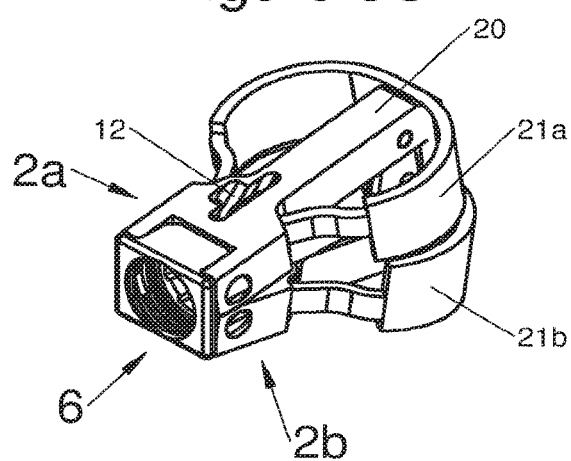
Figure 3D:
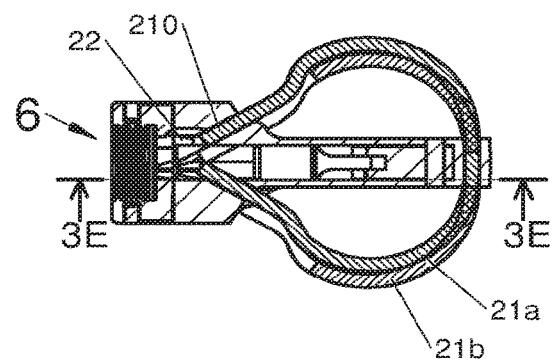
FIGS. 3D and 3E show section views, respectively, along the plane 3D-3D of FIG. 3B, and along the plane 3E-3E of FIG. 3D.
Figure 3E:
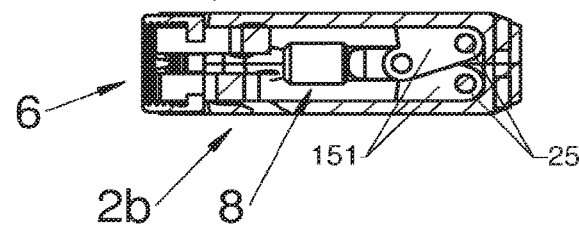
Figure 4A:
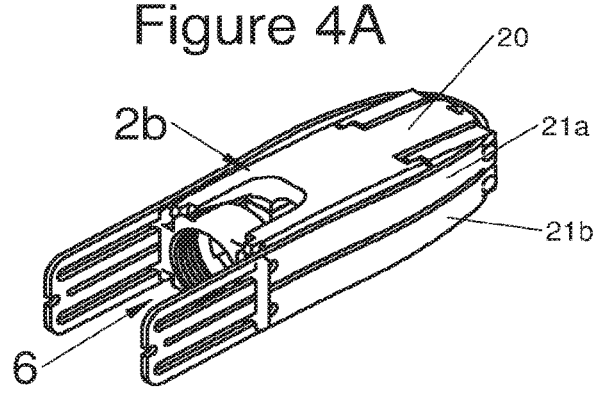
FIG. 4A shows a perspective view of an intervertebral implant according to an embodiment prior to lateral deployment of lateral expansion means.
Figure 4B:
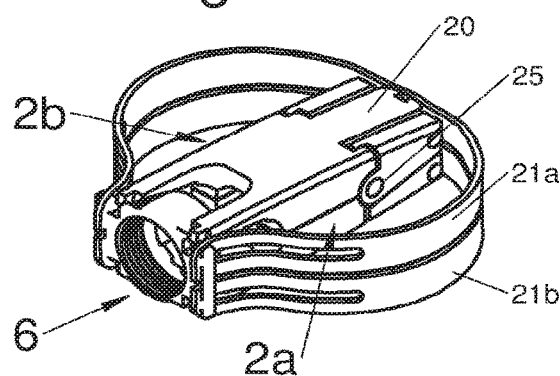
FIGS. 4B and 4C show perspective views of an intervertebral implant according to an embodiment after lateral deployment of lateral expansion means and comprising elongated arms, respectively, in folded-back position and in deployed position.
Figure 4C:
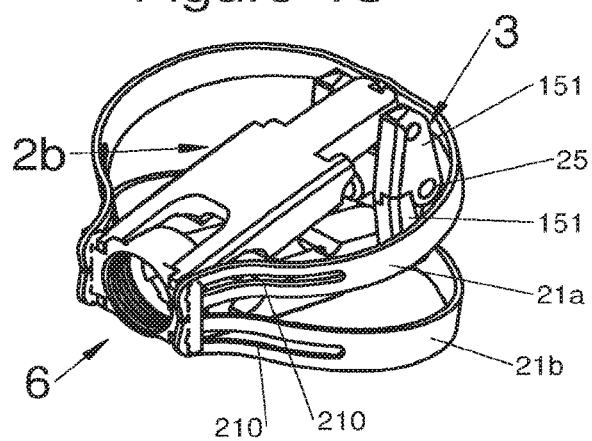
Figure 4D:
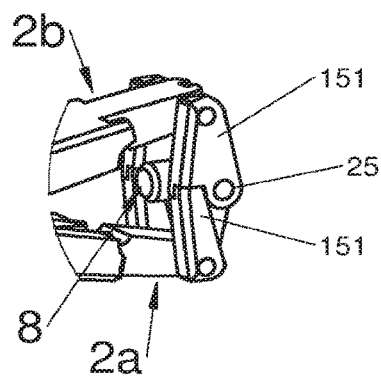
FIG. 4D shows a perspective view of expansion means when the elongated arms of the implant are deployed.
Figure 14A:
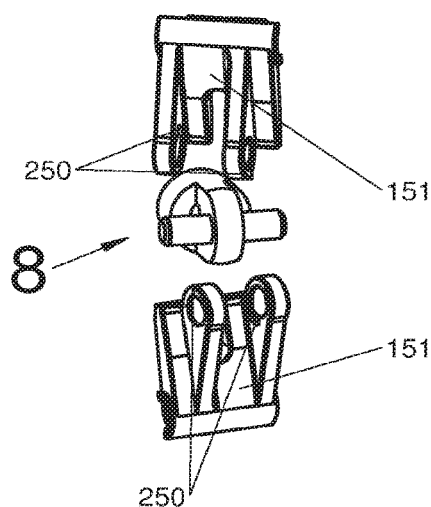
FIGS. 14A and 14C show perspective views of expansion means according to an embodiment, respectively, before and after assembly of said means.
Figure 14B:
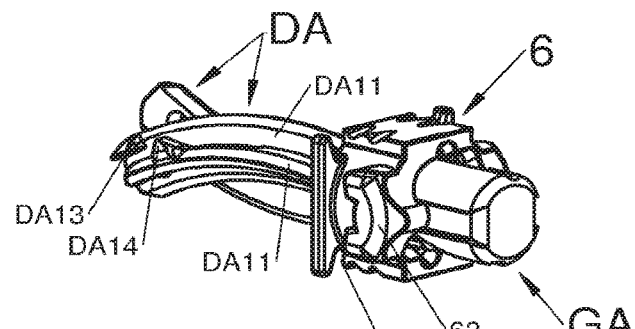
FIGS. 14B and 14D show perspective views of a baseplate of a vertebral implant according to an embodiment, respectively, before and after deployment of two anchoring devices.
Figure 14C:
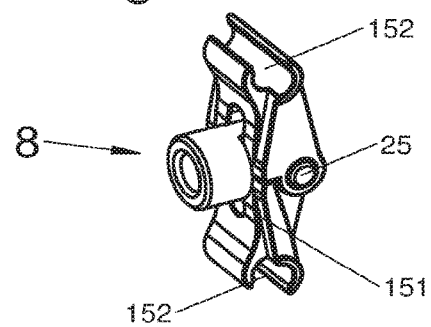
Figure 14D:
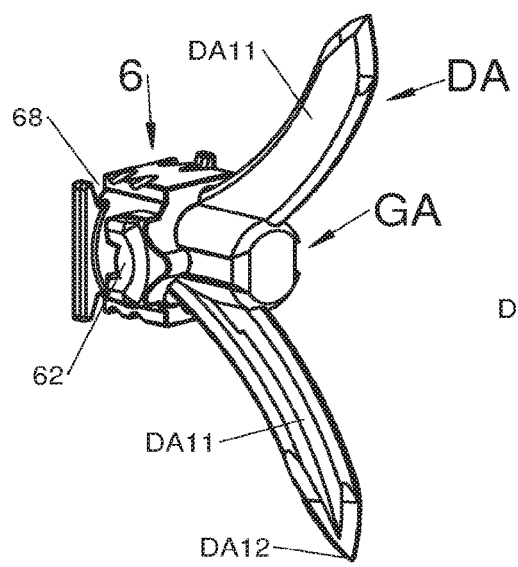
Figure 14E:
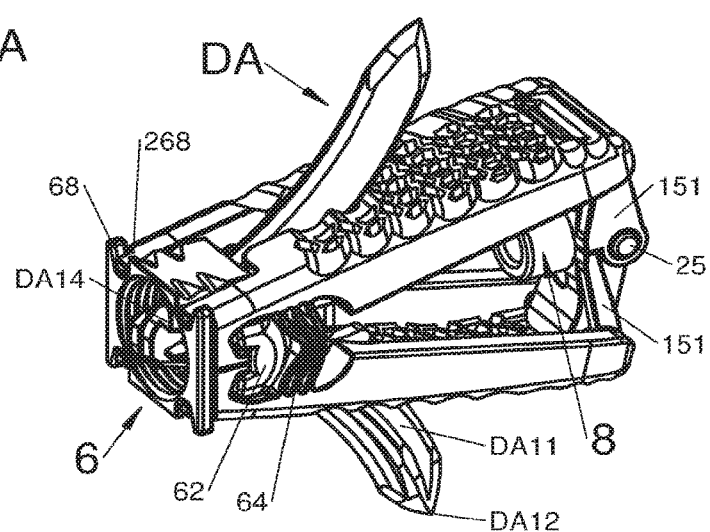
FIG. 14E shows a perspective view of the anchoring devices deployed via the implant.
Figure 15A:
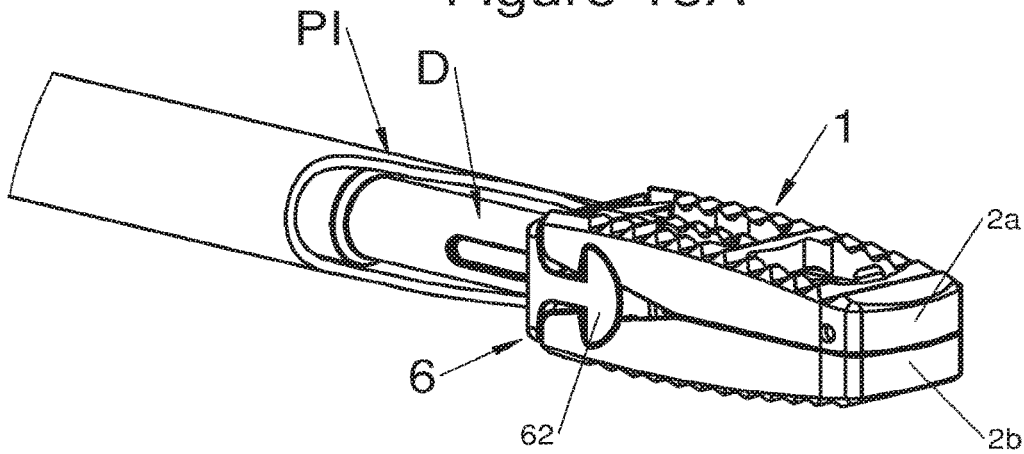
FIGS. 15A and 15B show perspective view of an intervertebral implant according to an embodiment, respectively, before and during deployment of the expansion means and elongated arms using instrumentation.
Figure 15B:
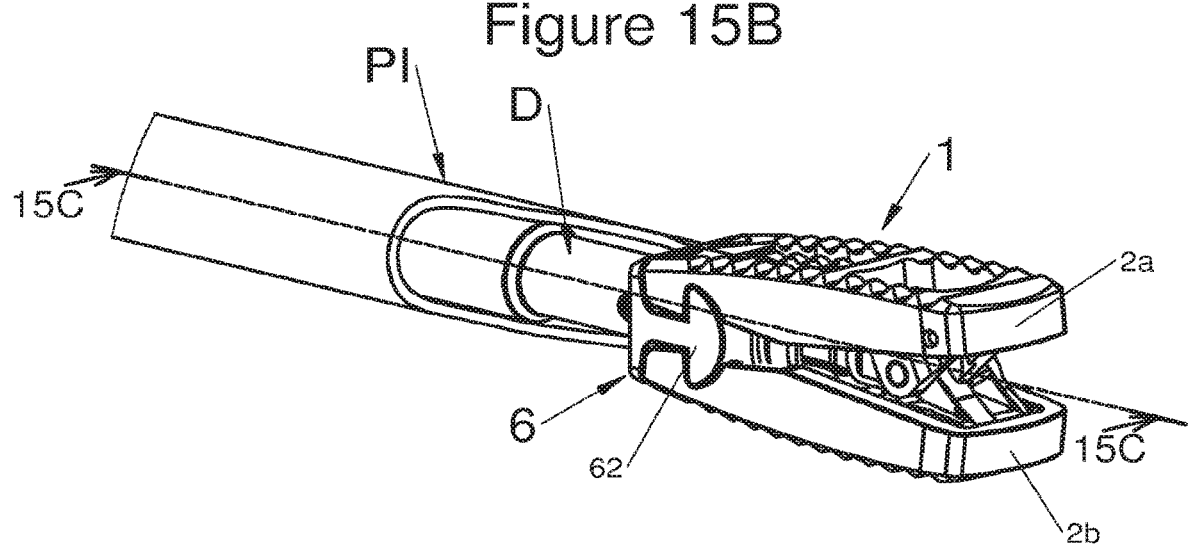
Figure 15C:
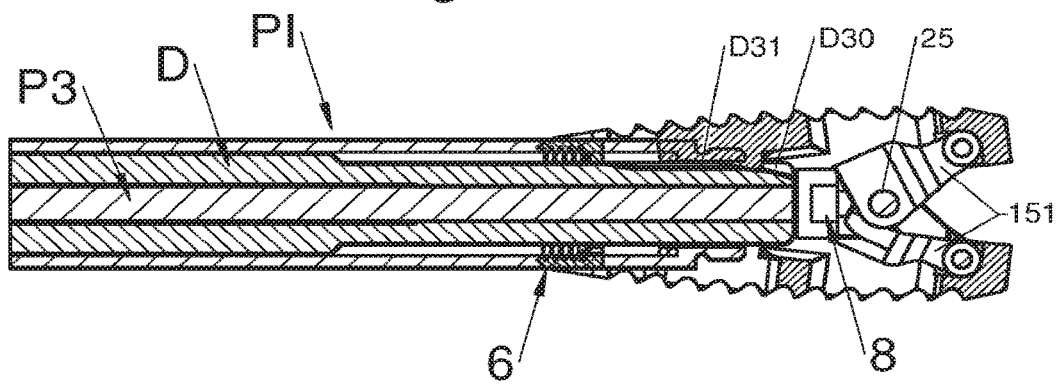
FIG. 15C shows a section view along the plane 15C-15C of FIG. 15B.

On the other hand, the present application describes various embodiments of a bone anchoring for the implant, and therefore details various types of bone anchoring, generally called "anchors" in the present application, even though they may also consist of a screw implanted by screwing (spiral rotation), or a device planted in the bone following a rectilinear translation or following a curved trajectory, for example as illustrated in FIG. 13C, 14E or 17C, or of a projecting portion capable of anchoring itself in bone after deployment of the implant between the intervertebral space, for example as shown in FIG. 2E. The term anchor is therefore used here only with reference to its anchoring function and it does not imply any limitation in shape or structure, with the exception of the fact that the anchor is preferably extended along a longitudinal axis which extends between a first end, designated here as the "distal end", designed to penetrate into a bone (generally a vertebra), and as second end, designated here as a "proximal end", designed in general to remain in the implant to retain it and to hold it in place. Thus, for the anchor (DA), the first end, so-called distal, is that intended to be inserted first and intended to penetrate into a vertebra to attach an implant. Various types of anchors may of course be used in various combinations in any embodiments. In addition, various types of anchors may be deployed in one of the embodiments described or suggested in this application, even if it is not expressly noted as a component of such an embodiment.

Thus, in certain embodiments, the implant (1) further comprises at least one anchoring device (DA) disposed via a passage (or a duct or an opening) located on at least one peripheral wall of the implant (1) and passing through at least one portion of said implant (1) to enter at least one vertebra (V) and fix said implant (1) onto said vertebra (V). In fact, in various embodiments, intersomatic implants fitted with bone anchors are preferred for use. But due to the bulk, the anchoring will preferably be selected from anchoring devices (DA) in the shape of a curved anchor as it allows implantation of the anchor by an approach formed substantially in the plane of the disc space, which may reduce the invasive character of the surgical operation of the implantation on the patient. For these types of deployment, intervertebral implants intended to be implanted in the disc space between the vertebrae and comprising at least one peripheral wall may be used, with a posterior or proximal end, comprising an opening for at least one passage, which may have a rectilinear shape (or curved, or another shape), dimensions and orientation complementary to the forms and dimensions of at least one anchoring device or anchor or screw (DA) comprising at least one elongated body (DA10) along a longitudinal axis extending between a distal end, and a proximal end, said body (DA10) being inserted in said passage, substantially in the plane of the implant (1), by sliding from said proximal part of the implant (1), said passage passing through the implant (1) from the periphery towards an upper or lower surface such that the distal end of said body (DA10) enters one of said adjacent vertebrae (V), while the proximal end stays in said passage or along the proximal surface and retains said implant (1) against said vertebra (V). In a preferred embodiment, the anchor will be generally rigid and will pass through the passage without deformation, but other embodiments using flexible or deformable anchors may be used. Generally, in this type of embodiment, said anchoring device (DA) is intended to be anchored in one of the vertebrae (V) so as to fix the implant (1) on/against this vertebra (V). In certain embodiments, said body (DA10) of the anchoring device (DA) may comprise at least one rib (DA11) or a second projection which will generally be disposed along the body (DA10). In certain embodiments, the rib or the projection may be fitted, i.e., cooperate with at least one groove provided in the passage of the implant (1) to receive the rib or the projection. In certain embodiments, the elongated arms (2a, 2b) of the implant (1) comprise at least one opening (12) capable of receiving at least partially the deployed anchoring device (DA), as shown for example in FIGS. 2A, 2B, 3B and 3C. In certain embodiments, the passage may open along a portion or the totality of the passage path through the implant, but in most of the preferred embodiments, the passage will have at least a portion of the passage forming a closed space open at its opposite ends.

In certain embodiments, said rib (DA11) is preferably intended at least to limit (or even prevent) transversal displacement of the anchor (DA) (and therefore also of the implant) relative to the vertebra (V). The rib may also be configured and deployed to stiffen the anchor (DA). For example, FIG. 13C or 14E show anchoring devices (1) fitted with at least one rib (16). Also, for example in FIG. 13C, the anterior or distal end of the body (DA10) of the anchor (DA) has substantially the shape of a bevel or chamfer or bullet point (DA12) to optimize penetration of the anchor (DA) in the vertebrae (V).

In certain embodiments, the anchoring devices (DA) may be implanted easily via the baseplate (6) of the implant (1) in the vertebrae (V). Due to this, the baseplate (6) participates in guiding of the deployment of the anchors of the anchoring device (DA) and the baseplate (6) may comprise on the one hand at least one guide groove adapted to at least partially guide the anchoring device (DA). In certain embodiments, the baseplate (6) may comprise at least one orifice adapted to receive at least partially an anchoring guide (GA) of the anchoring device (DA). In fact, the baseplate (6) comprises for example and non-limiting, at least one opening whereof the walls are complementary to those of the anchor, for example by forming grooves intended to match the contours of the anchor(s) which the baseplate is designed to receive. FIGS. 14B and 14D show examples of such guiding of the anchors by the baseplate with an anchoring guide (DA) facilitating guiding of the anchors in the baseplate via an orifice and the anchoring guide participates in indexing of the orientation of the anchors by way of complementarity of shape of the peripheral wall of the guide (DA) with the inner wall of the opening in the baseplate (6). Complementarity between the guide (GA) and the baseplate (6), with at least one rib in the peripheral wall of the guide (GA) which cooperates with at least one projection in the opening of the baseplate (6) enables indexing the orientation of the guide (GA) and anchors (DA) via the baseplate (6). It is evident that the term "guide" has a functional definition and that the examples of structures provided by way of example here must not be considered as limiting, but that the guide has necessarily a shape to ensure its guiding function.

In various embodiments, locking means of the anchors are provided to help in securing the anchors and attaching the implantation attachment of the implant in the bone tissue. After anchoring in the bone tissue, unwanted movements of the anchors, for example during movements of the patient, cause risks of these anchors receding and exiting from the bone, which may cause considerable damage for the patient. It is therefore useful to provide at least one mechanism securing bone anchoring, as example by locking the anchors. Various types of locking means are possible, as example for obtaining reciprocal locking of anchors together and/or locking of at least one anchor with another element or the implant. For example, the anchoring device (DA) provides for locking means, such as a tab (DA13) and/or an abutment (DA14), locking to a clip disposed on a proximal end of the baseplate (6), for example as shown in FIGS. 14B and 14E. In certain embodiments, the proximal end of the body (20) of the implant comprises and extension (268) capable of housing itself in a cavity (68) of the clip of the baseplate (6) allowing the implant to be stabilized after deployment of said arms, such for example as shown in FIG. 14E. In certain embodiments, the baseplate (6) comprises a profile (62) capable of clipping itself into an opening (64) in the proximal end of the body (20) of the implant, so as to lock the baseplate on the proximal end of the body of said implant after deployment of the arms, as shown for example in FIG. 14E.

Figure 10A:
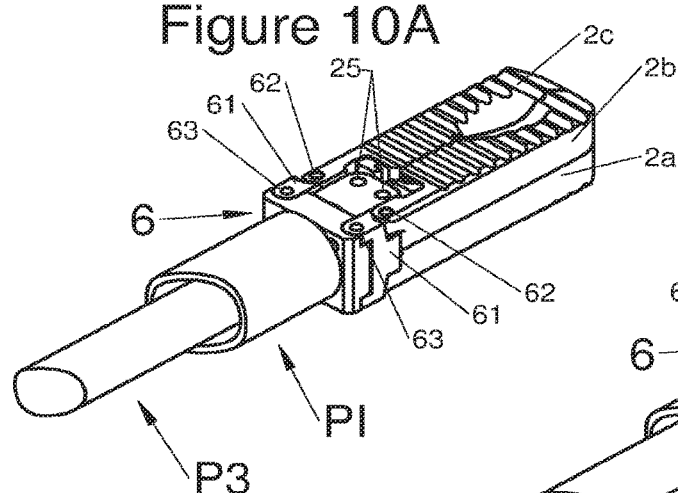
FIGS. 10A, 10B and 10C show perspective views of an intervertebral implant according to an embodiment, respectively, before, during and after deployment of expansion means and elongated arms using instrumentation.
Figure 10B:
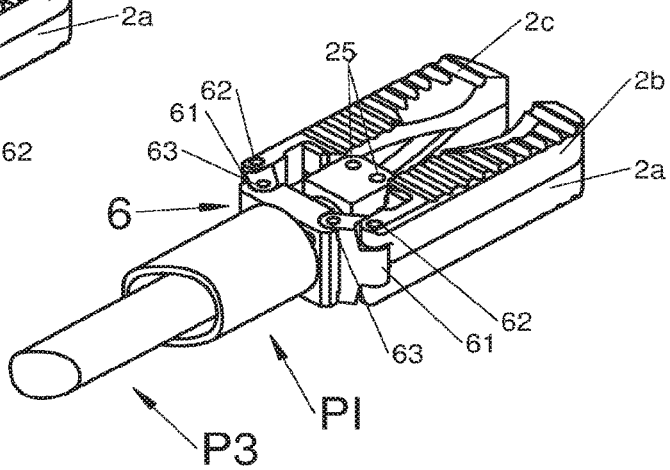
Figure 10C:
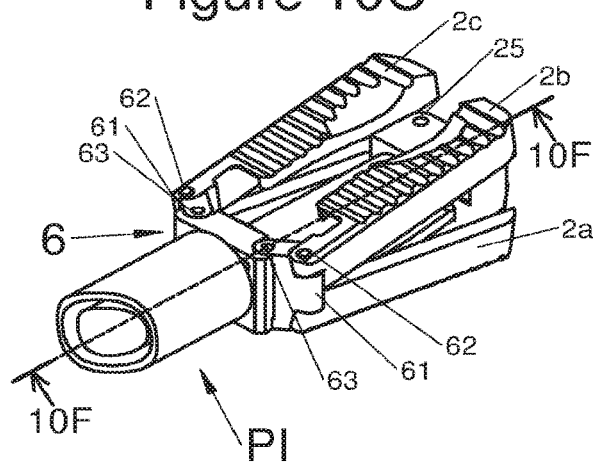
Figure 10D:
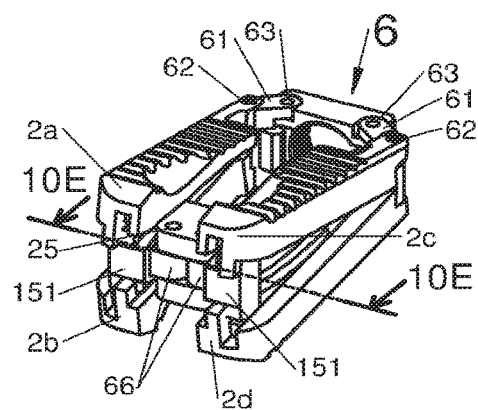
FIG. 10D shows a view, respectively, in perspective of the implant comprising the deployed elongated arms.
Figure 10E:
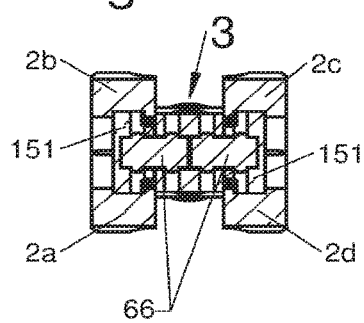
FIGS. 10E and 10F show section views, respectively, along the plane 10E-10E of FIG. 10D and along the plane 10F-10F of FIG. 10C.
Figure 10F:
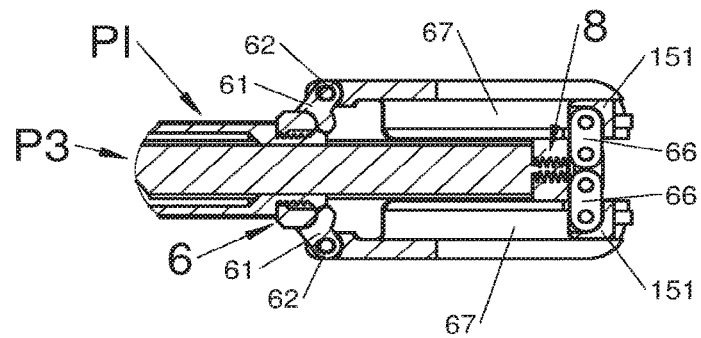
Figure 11A:
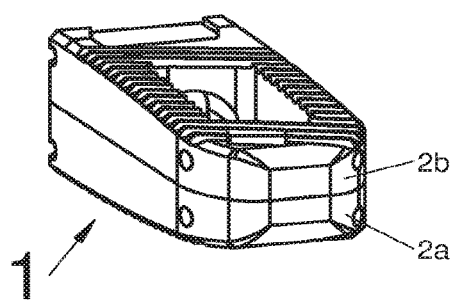
FIGS. 11A and 11B show perspective views of an intervertebral implant according to an embodiment comprising elongated arms, respectively, in folded-back position and in deployed position.
Figure 11B:
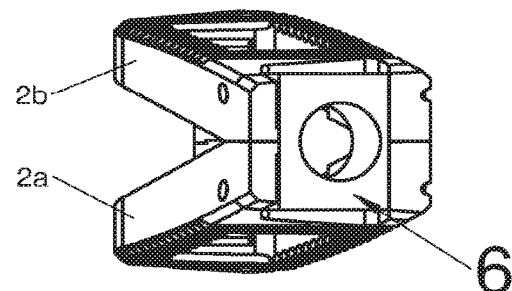
Figure 11D:
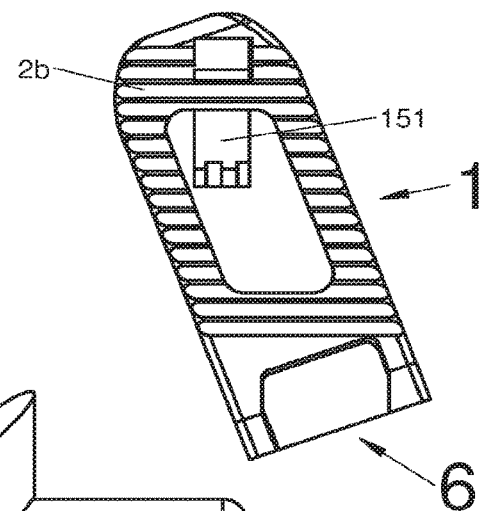
FIG. 11D shows a top view of FIG. 11B.
Figure 11C:
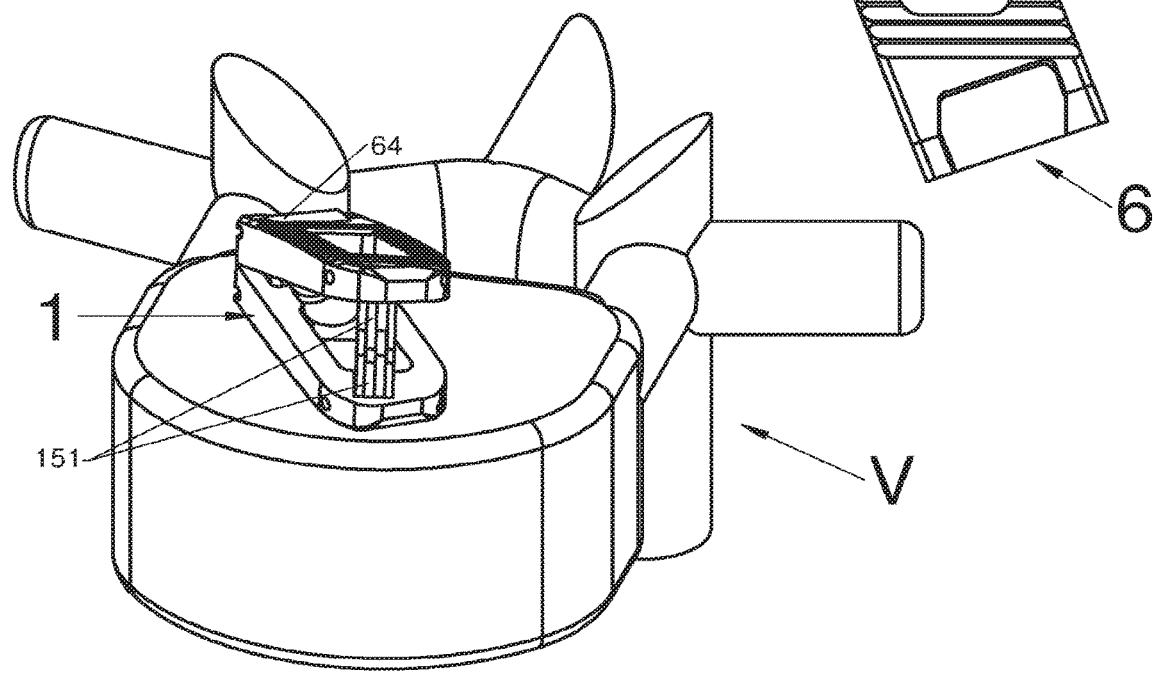
FIG. 11C shows a perspective view of the same deployed implant disposed on a vertebra.
Figure 16A:
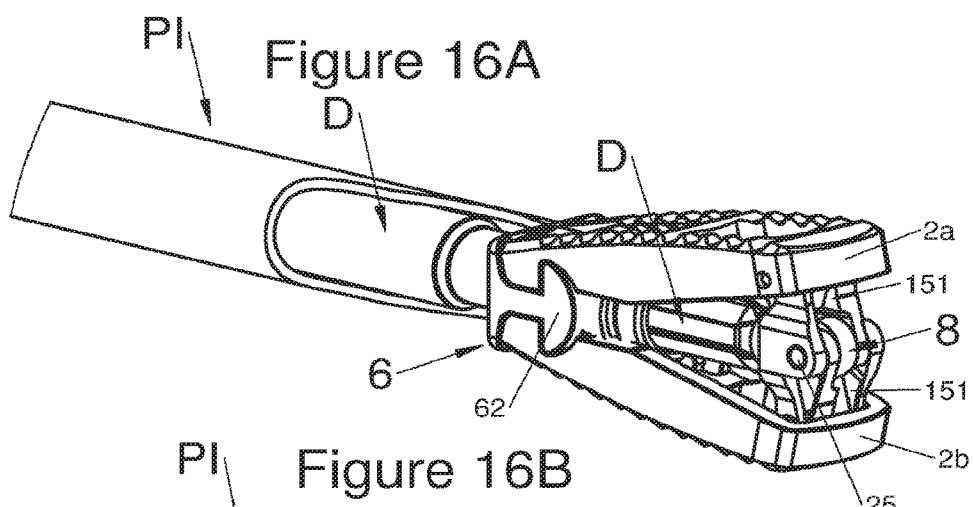
FIGS. 16A and 16B show perspective partial views of an intervertebral implant according to an embodiment after deployment of the elongated arms, respectively, before and after loading of the graft using instrumentation (in which an implant holder tube of the instrumentation is shown in section)
Figure 16B:
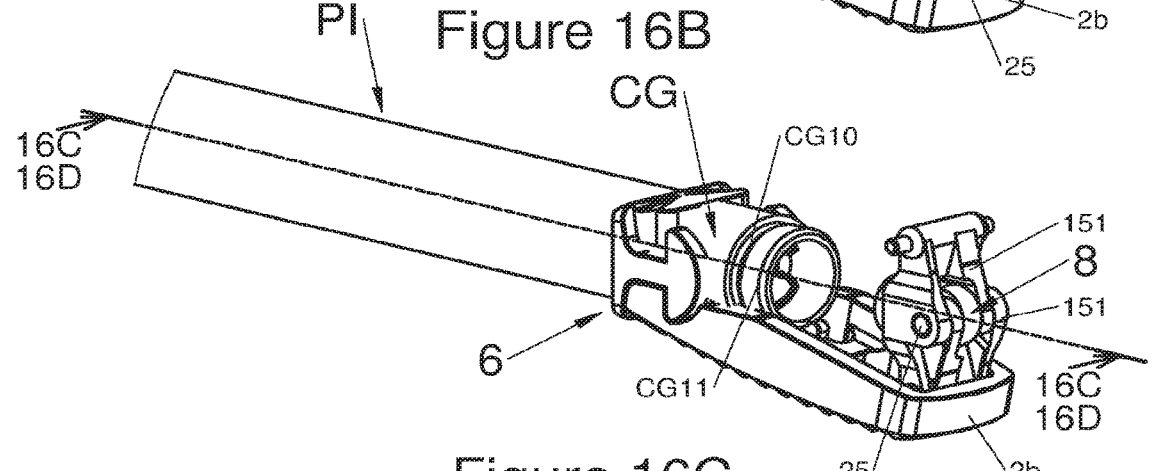
Figure 16C:
FIGS. 16C and 16D show section views along the plane 16C-16C and 16D-16D of FIG. 16B, respectively, before and during impaction of the graft in the implant.
Figure 16D:
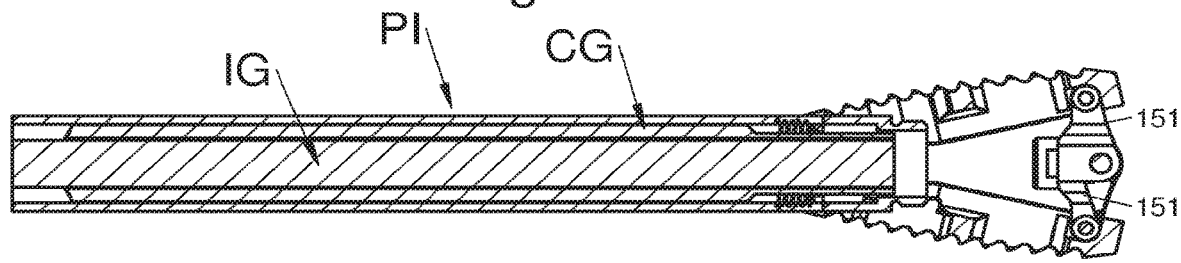

Various embodiments of the present application concern instrumentation for insertion of an intervertebral implant in a treatment zone. Certain embodiments are described with reference to the insertion in the spine and preferably for fastening of this implant in the adjacent vertebral structures. Such instrumentation comprises at least one implant holder tube (PI) and a deployer (D) comprising a connection rod (P3). The implant holder tube (PI) is capable of being fixed on the baseplate (6) of the implant (1) and guiding it towards the vertebra (V). This implant holder tube (PI) comprises holding means complementary to hooking means present on the baseplate (6) of the implant (1). Various types of holding means and hooking means are known from the prior art, such as for example rods of the implant holder, threaded or not, penetrating in passages, tapped or not, of the implant, or arms of the implant holder cooperating with lateral edges and/or upper and/or lower faces of the implant, for example by inserting said arms in grooves of the implant (or for example hooks on a hollowed engagement structure, or openings on another structure). For example FIG. 10A, 10F, 12A or 13A show examples of tapping capable of cooperating with a threaded end of the implant holder tube (PI) of the instrumentation. In certain embodiments, a deployer (D) is used in the implant holder tube (PI) to guide the implant (1) and trigger deployment or expansion of the arms of the implant in the intervertebral space. In certain embodiments, a distal end of the deployer (D) may comprise a pre-expansion system (D3, D31) of the implant (1) prior to actuating the deployer, for example and without limitation by pushing manual, for the final expansion of the implant in the intervertebral space. Indeed, the connection rod (P3) contained in the deployer (D) is fixed to the hooking means (8) of the implant (1) so as to actuate the expansion means for deployment or expansion of the elongated arms (2a, 2b, 2c, 2d). As well as the implant holder tube and the baseplate, the connection rod comprises complementary holding means to the hooking means (8) of the expansion means of the implant. FIG. 10F shows an example of tapping comprised in the hooking means (8) and capable of cooperating with a threaded end of the connector (P3) of the instrumentation. In certain embodiments, the deployer (D) and the connection rod (P3) are disposed in the implant holder tube (PI) to receive thrust or shock, for example by an impacter, so that the anterior or distal end of the implant (1) is able to penetrate into the intervertebral space and/or deliver the graft (G) through the charger (CG) into the implant (1). In certain embodiments, the charger (CG) may define the dose or the appropriate volume of bone graft or substitute to be delivered with respect to the volume of the implant. For example, as shown in FIGS. 16B and 16C, the charger (CG) may be a tube comprising a duct (CG12) for receiving, for example, a graft or a substitute, and may further comprise an end (CG10) having hooking means (CG11) complementary to the hooking means (8) of the implant (1), so as to immobilize the attachment of the charger in the implant and obtain a reliable impaction of the graft or of the substitute.

In certain embodiments, the surgical instrumentation comprises at least one charger (CA, CG) capable of receiving anchoring devices (DA) and/or the graft (G) and sliding in the implant holder tube (PI). The charger is fitted with a guiding surface (C0) for receiving an impacter (IG) for pushing said anchoring devices (DA) and/or said graft (G) via the implant holder tube (PI) towards the vertebrae (V). This embodiment has the advantage of facilitate the impacting of the anchoring devices (DA) and/or of the graft (G), via the implant holder tube (PI) towards the vertebrae (V), via an impacter for allowing a reliable, stable and minimally invasive anchoring.

In certain embodiments, the instrumentation further comprises an implantation pistol (P) including a handle (PPI) capable of connecting with the implant holder tube (PI) via connection means (CPI) so as to implant at least one implant (1), an anchoring device (DA) and/or a graft (G) towards the vertebra (V). In fact, as shown for example in FIGS. 20A to 20E, the connection means (CPI) is fixed on the one hand to the implant holder tube (PI) by its anterior end, and on the other hand to the handle (PPI) of the pistol (P) by its posterior end. Indeed, the posterior end of the connection means (CPI) comprises at least one groove (PPI2) capable of engaging with at least one clip or a tab (PPI1) disposed in an opening (PP12) of the handle (PPI) of the pistol. In this way, with actuating of the latch (L) of the pistol (P), the clip or tab (PPI1) of the handle (PPI) disengages from the groove (PPI2) of the connection means (CPI) so as to free the implant holder tube (PI).

In various embodiments, the instruments, such as the deployer (D), the charger (CA, CG) or the impacter (IG), may be coupled and uncoupled successively onto and from the pistol (P) during implantation. In fact, different types of instruments, for example and non-limiting an implant deployer, a graft impacter, an anchor impacter or other types of instruments, may be mounted successively or not on the pistol during implantation of the implant between the intervertebral space. Because of this, the handle (PPI) of the pistol (P) may be connected and disconnected several times as needed by the surgeon with or without the instruments (D, P3, CA, CG, IG) in the implant holder tube (PI). This embodiment has the advantage of facilitating the implantation of an intervertebral implant in the intervertebral space using the pistol. In fact, the pistol successively performs implantation of an intervertebral implant, the anchoring devices and the graft by the same instrumentation. The pistol is adapted to use of several types of charger, i.e., at the same time an anchoring device charger and a graft charger. The pistol is also adapted to fast and easy assembly and disassembly with other implantation instruments such as the deployer (D), the charger (CA, CG) or the impacter (IG). In this way, this embodiment lets the surgeon perform all the steps of a surgical operation for lordosis, i.e., from implantation of the intervertebral implant to loading of the graft to facilitate arthrodesis, by optimizing time and costs required for such an operation.

Figure 21A:
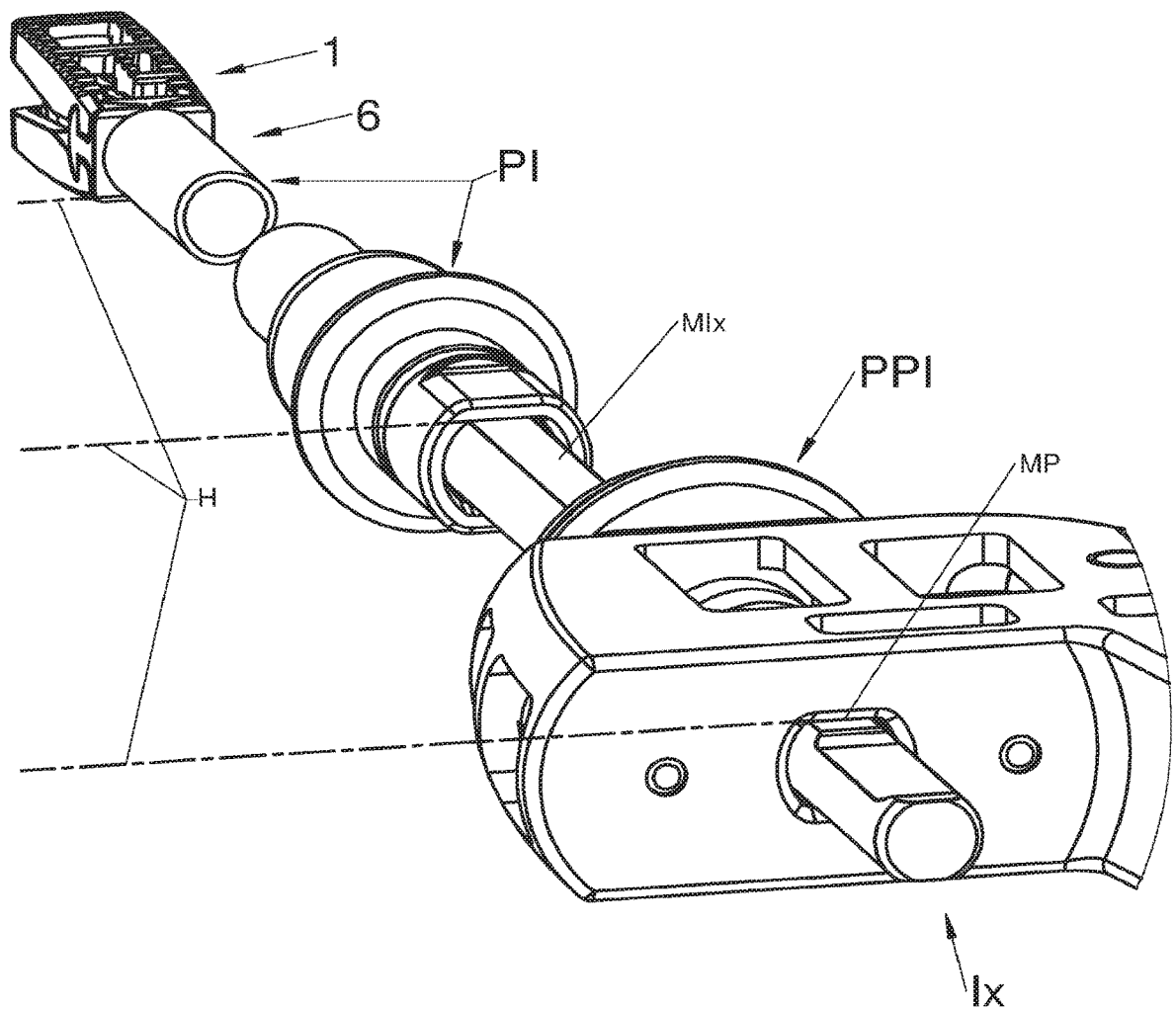
FIG. 21A shows a perspective view of alignment of the pistol, instrumentation and intervertebral implant to be implanted between two adjacent vertebrae.

Certain embodiments relate to a preparation method for the implantation of an intervertebral implant (1) in at least one vertebra (V). As example, the aim of various embodiments is good stabilization of the spine in view of arthrodesis, and the implant preferably comprises expansion means for deployment of the arms (2a, 2b, 2c, 2d) of the implant (1) along the secondary axis (Y) and/or the tertiary axis (Z). The method therefore comprises an insertion step of at least one intervertebral implant and/or an anchoring step of this implant with at least one anchoring device (DA) and/or a loading step of the graft (G) in situ, using implantation instrumentation (P, PI, P3, D, CA, CG, IG) which may comprise a pistol (P) or not. In the case of implantation with the pistol (P), the intervertebral implant (1) is pre-deployed before being inserted into the intervertebral space by the implant holder tube (PI). In fact, the action on the latch (L) of the pistol (P) causes the clip or the tab (PPI1) to disengage from the handle (PPI) of the groove (PPI2) of the connection means (CPI) so as to free the implant holder tube (PI) and exert slight thrust enabling pre-deployment of the implant in the intervertebral space. Next, the deployer (D) and the connector (P3) are mounted on the pistol (P) so as to actuate the expansion means of the implant and fully deploy the arms (2a, 2b, 2c, 2d) of the implant in the intervertebral space. Once the implant (1) is inserted in the intervertebral space, other instruments may be mounted on the pistol to reinforce the stability of the implant. In fact, for example and non-limiting, at least one anchoring device (AA) and an anchor impacter may be mounted on the pistol (P) for implanting said anchoring device (DA) via the implant (1) in at least one vertebra (V). Also, for example and non-limiting, a graft (G) and a graft impacter (IG) may be mounted on the pistol (P) for inserting the graft in the implant (1) and reinforcing bone fusion. On the other hand, as shown for example in FIG. 21A, the use of the pistol (P) aligns the flat spot (MP) and the handle (PPI) of the pistol (P) with the implant holder tube (PI) and the implant (1) as per optimal indexation to obtain easy and rapid implantation of the implant in the intervertebral space.

The present application describes various technical features and advantages in reference to the figures and/or various embodiments.

One skilled in the art will understand that the technical features of a given embodiment may in fact be combined with characteristics of another embodiment unless the opposite is explicitly mentioned or unless it is obvious that these characteristics are incompatible or the combination fails to provide a solution to at least one of the technical problems mentioned in the present application.

Further, the technical features described in a given embodiment may be isolated from the other features of that embodiment unless the opposite is explicitly mentioned.

It must be evident for skilled persons that the present disclosure enables embodiments in many other specific forms without going beyond the field of application of the disclosure as claimed. Consequently, the present embodiments must be considered by way of illustration, but may be modified in the field defined by the scope of the appended claims, and the disclosure must not be limited to the details given hereinabove.

The invention claimed is:

1. An intervertebral implant comprising a body extending longitudinally along a primary axis, the intervertebral implant comprising:
   a baseplate disposed at a proximal end of the body;
   an elongated arm including a superior arm and an inferior arm disposed along the primary axis and each including a vertebral support surface, the elongated arm being articulable relative to the baseplate such that the intervertebral implant comprises a collapsed position in which the elongated arm is in a first spatial position and a deployed position in which the elongated arm is in a second spatial position that differs from the first spatial position along both a secondary axis and a tertiary axis;
   an expansion mechanism engaging the superior and inferior arms; and
   an insert including an elongate hollow externally threaded cylinder, wherein during implantation of the implant between adjacent vertebrae, a deployer engages the baseplate interiorly of the superior and inferior arms to guide the implant into a desired position between the adjacent vertebrae and a connection rod is telescopically received within the deployer and elongate hollow externally threaded cylinder to engage the body of the implant to articulate the elongated arm relative to the baseplate and expand the intervertebral implant along the secondary axis and the tertiary axis.

2. The intervertebral implant of claim 1, wherein the expansion mechanism comprises a hooking device that rotatably engages the superior and inferior arms and wherein the insert translates the expansion mechanism along the primary axis.

3. The intervertebral implant of claim 1, wherein the baseplate is configured to engage an implant holder tube during deployment of the intervertebral implant between adjacent vertebrae, wherein the implant holder tube is configured to telescopically receive the deployer and engage the body interiorly of the superior and inferior arms, wherein the elongated arm comprises a plurality of elongated arms including a plurality of superior arms and a plurality of inferior arms disposed along the primary axis and each including a vertebral support surface, wherein the expansion mechanism includes a pair of branches, and wherein the expansion mechanism includes a guide element disposed between the pair of branches.

4. The intervertebral implant of claim 3, wherein each branch of the pair of branches pivots relative to the guide element during deployment of the plurality of elongated arms from the collapsed position to the deployed position.

5. The intervertebral implant of claim 3, wherein the guide element includes a separation element that cooperates with the pair of branches to enable separation of the pair of branches during deployment of the plurality of elongated arms from the collapsed position to the deployed position.

6. The intervertebral implant of claim 3, wherein each elongate arm of the plurality of elongated arms includes a guide surface opposite the vertebral support surface.

7. The intervertebral implant of claim 6, wherein each branch of the pair of branches includes projections that engage guide surfaces on two elongated arms of the plurality of elongate arms.

8. The intervertebral implant of claim 7, wherein the guide surfaces include grooves to receive the projections.

9. The intervertebral implant of claim 3, wherein the plurality of elongated arms are coupled to the baseplate via at least one of pins, hooks, rings, and linkages to enable articulation of the plurality of elongate arms relative to the baseplate.

10. The intervertebral implant of claim 1, wherein the insert is a receivable within a threaded bore in a proximal surface of the baseplate, and wherein the insert includes cavities through a sidewall of the elongate hollow externally threaded cylinder.

11. An intervertebral implant comprising:
   a baseplate forming a proximal end of the intervertebral implant;
   a superior arm articulable from a coupling point on a superior portion of the baseplate, the superior arm extending along a primary axis and articulable in both a secondary axis and a tertiary axis;
   an inferior arm articulable from a coupling point on an inferior portion of the baseplate, the inferior arm extending along the primary axis and articulable in both the secondary axis and the tertiary axis; and
   an expansion mechanism including a pair of lateral branches operable upon engagement of an insert to translate the expansion mechanism along the primary axis causing expansion of the superior arm and the inferior arm along the secondary axis and the tertiary axis, wherein the insert includes an elongate hollow externally threaded cylinder and wherein, during implantation of the implant between adjacent vertebrae, an elongated deployer engages the baseplate between the superior and inferior arms to guide the implant into a desired position between the adjacent vertebrae and a connection rod is telescopically received within the elongated deployer and elongate hollow externally threaded cylinder to engage the elongate hollow externally threaded cylinder, rotation of the elongate hollow externally threaded cylinder by the connection rod translating the expansion mechanism along the primary axis.

12. The intervertebral implant of claim 11, wherein the baseplate is configured to engage an implant holder tube during deployment of the intervertebral implant between adjacent vertebrae, wherein the implant holder tube is configured to telescopically receive the deployer and engage a body of the intervertebral implant interiorly of the superior and inferior arms, and wherein the expansion mechanism includes a guide element disposed between the pair of lateral.

13. The intervertebral implant of claim 12, wherein the superior arm comprises a plurality of superior arms, wherein the inferior arm comprises a plurality of inferior arms, wherein a plurality of elongated arms includes the plurality of superior arms and the plurality of inferior arms disposed along the primary axis and each including a vertebral support surface, and wherein each branch of the pair of lateral branches pivots relative to the guide element during deployment of the plurality of superior arms and the plurality of inferior arms from a collapsed position to a deployed position.

14. The intervertebral implant of claim 13, wherein the guide element includes a separation element that cooperates with the pair of lateral branches to enable separation of the pair of lateral branches during deployment of the plurality of superior arms and the plurality of inferior arms from a collapsed position to a deployed position.

15. The intervertebral implant of claim 13, wherein each arm of the plurality of superior arms and the plurality of inferior arms includes a guide surface opposite a vertebral support surface, wherein the vertebral support surface is external to the intervertebral implant and wherein each branch of the pair of lateral branches includes a superior projection and an inferior projection that engage guide surfaces on opposing arms of the plurality of superior arms and the plurality of inferior arms.

16. The intervertebral implant of claim 13 wherein guide surfaces include grooves to receive a superior projection and inferior projection.

17. The intervertebral implant of claim 13, wherein the plurality of superior arms and the plurality of inferior arms are coupled to the baseplate via at least one of pins, hooks, rings, and linkages to enable articulation relative to the baseplate.

18. The intervertebral implant of claim 11, wherein the baseplate is configured to engage an implant holder tube during deployment of the intervertebral implant between the adjacent vertebrae, wherein the implant holder tube is configured to telescopically receive the deployer and engage a body of the intervertebral implant interiorly of the superior and inferior arms, wherein the insert comprises a hooking device, and wherein the hooking device rotatably engages the superior and inferior arms and.

19. An intervertebral implant comprising a body extending longitudinally along a primary axis, the intervertebral implant comprising:

a baseplate disposed at a proximal end of the body and configured to engage an implant holder tube during deployment of the intervertebral implant between adjacent vertebrae;

opposing first and second elongated arms disposed along the primary axis and each including a vertebral support surface, each of the first and second elongated arms articulable relative to the baseplate such that the intervertebral implant comprises a collapsed position in which the first and second elongated arms are close to each other and a deployed position in which the first and second elongated arms are separated from each other along a secondary axis and a tertiary axis;

a hooking device pivotably engaging the first and second elongated arms; and an insert including an externally threaded hollow cylinder, wherein, during implantation, an elongated deployer is telescopically received within the implant holder tube to engage the insert interiorly of the opposing first and second elongated arms and guide the implant into a desired position between the adjacent vertebrae and a connection rod is telescopically received within the elongated deployer and externally threaded hollow cylinder to engage the hooking device to cause articulation of the first and second elongated arms relative to the baseplate to expand the intervertebral implant along the secondary axis and the tertiary axis.

* * * * *

UNITED STATES PATENT AND TRADEMARK OFFICE
CERTIFICATE OF CORRECTION

| | | |
|---|---|---|
| PATENT NO. | : 12,213,892 B2 | Page 1 of 1 |
| APPLICATION NO. | : 17/888895 | |
| DATED | : February 4, 2025 | |
| INVENTOR(S) | : Pierre Bernard et al. | |

It is certified that error appears in the above-identified patent and that said Letters Patent is hereby corrected as shown below:

In the Claims

At Column 19, Line 24, after "cylinder to engage the" insert --expansion mechanism to cause translation of the expansion mechanism relative to the-- therein.

At Column 20, Line 46, after "lateral" insert --branches-- therein.

Signed and Sealed this
Fourteenth Day of October, 2025

John A. Squires
*Director of the United States Patent and Trademark Office*